(12) United States Patent
Fournie-Zaluski et al.

(10) Patent No.: US 8,466,309 B2
(45) Date of Patent: Jun. 18, 2013

(54) AMINO ACID DERIVATIVES, METHOD FOR PREPARING SAME, AND THERAPEUTIC USE THEREOF

(76) Inventors: Marie-Claude Fournie-Zaluski, Paris (FR); Hervé Poras, Bailly (FR); Bernard Roques, Paris (FR)

( * ) Notice: Subject to any disclaimer, the term of this patent is extended or adjusted under 35 U.S.C. 154(b) by 0 days.

(21) Appl. No.: 12/991,999

(22) PCT Filed: May 13, 2009

(86) PCT No.: PCT/EP2009/055787
§ 371 (c)(1),
(2), (4) Date: Nov. 10, 2010

(87) PCT Pub. No.: WO2009/138436
PCT Pub. Date: Nov. 19, 2009

(65) Prior Publication Data
US 2011/0071218 A1    Mar. 24, 2011

(30) Foreign Application Priority Data

May 13, 2008   (FR) ..................... 08 53092

(51) Int. Cl.
C07C 69/74      (2006.01)
C07C 321/00     (2006.01)
C07C 323/00     (2006.01)
C07C 381/00     (2006.01)
A01N 43/16      (2006.01)

(52) U.S. Cl.
USPC ............................ 560/121; 560/147; 514/454

(58) Field of Classification Search
None
See application file for complete search history.

(56) References Cited

U.S. PATENT DOCUMENTS

| | | |
|---|---|---|
| 4,407,794 A | 10/1983 | Roques et al. |
| 4,426,391 A | 1/1984 | Alexander et al. |
| 4,513,009 A | 4/1985 | Roques et al. |
| 4,618,708 A | 10/1986 | Roques et al. |
| 4,738,803 A | 4/1988 | Roques et al. |
| 4,985,406 A | 1/1991 | Charpentier et al. |
| 5,190,921 A | 3/1993 | Roques et al. |
| 5,491,169 A | 2/1996 | Roques et al. |
| 5,591,891 A | 1/1997 | Fournie-Zaluski et al. |
| 5,741,781 A | 4/1998 | Roques et al. |
| 5,801,274 A | 9/1998 | Fournie-Zaluski et al. |
| 6,136,842 A | 10/2000 | Deprez et al. |
| 6,340,708 B1 | 1/2002 | Llorens-Cortes et al. |
| 6,391,866 B1 | 5/2002 | Roques et al. |
| 6,518,260 B1 | 2/2003 | Fournie-Zaluski et al. |
| 6,716,852 B2 | 4/2004 | Roques et al. |
| 7,056,735 B2 | 6/2006 | Jacotot et al. |
| 7,160,982 B2 | 1/2007 | Roques et al. |
| 7,169,574 B2 | 1/2007 | Roques et al. |
| 7,205,435 B2 | 4/2007 | Roques et al. |
| 7,235,687 B2 | 6/2007 | Fournie-Zaluski et al. |
| 7,582,797 B2 | 9/2009 | Roques et al. |
| 7,642,051 B2 | 1/2010 | Jacotot et al. |
| 2002/0055463 A1 | 5/2002 | Garbay et al. |
| 2002/0061840 A1 | 5/2002 | Roques et al. |
| 2004/0072146 A1 | 4/2004 | Jacotot et al. |
| 2006/0135602 A1 | 6/2006 | Fournie-Zaluski et al. |
| 2009/0012153 A1* | 1/2009 | Roques et al. .............. 514/438 |
| 2009/0131509 A1 | 5/2009 | Roques et al. |
| 2009/0208993 A1 | 8/2009 | Fournie-Zaluski et al. |

FOREIGN PATENT DOCUMENTS

| | | |
|---|---|---|
| EP | 0 262 053 | 9/1987 |
| FR | 2 518 088 | 6/1983 |
| FR | 2 605 004 | 4/1988 |
| FR | 2 651 229 | 3/1991 |
| FR | 2 755 135 | 4/1998 |
| FR | 2 777 780 | 10/1999 |
| FR | 2892413 | * 4/2007 |
| WO | WO 2007/048787 | 5/2007 |

OTHER PUBLICATIONS

Barcelo, et al: "Alkyl 1-Chloroalkyl Carbonates: Reagents for the Synthesis of Carbamates and Protection of Amino Groups"; SNPE, centre de Recherche du Bouchet, Aug. 1986; p. 627.

Stein, et al: "Local Analgesic Effect of Engogenous Opioid Peptides"; The Lancet, vol. 342, Aug. 7, 1993, pp. 321-324.

Roques, et al: "Neutral Endopeptidase 24.11: Structure, Inhibition, and Experiemental and Clinical Pharmacology"; Pharmacological Reviews, vol. 45, No. 1, (1993) The American Society for Pharmacology and Experiemental Therapeutics, pp. 87-146.

Millan: "The Induction of Pain: An Integrative Review"; Progress in Neurobiology, vol. 57 (1999), pp. 1-164.

(Continued)

*Primary Examiner* — Susanna Moore
*Assistant Examiner* — Jennifer C Sawyer
(74) *Attorney, Agent, or Firm* — Harness, Dickey & Pierce, P.L.C.

(57) ABSTRACT

The disclosure relates to novel compounds of the formula (I) $R_1NH$—$CH(R_2)CH_2$—S—S—$CH_2$—$C(R_3)(R_4)$—CONH—$C(R_5)(R_6)$—$COOR_7$, in which $R_1$ is a (acyloxy) alkyl carbamate-$C(O)$—O—$C(R_8)(R_9)$—$OC(O)$—$R_{10}$ group; $R_2$ is a hydrocarbon chain, a methylene radical substituted by a heterocycle, $R_4$ is a hydrogen atom and $R_3$ is a phenyl or benzyl radical, a heteroaryl, a methylene group substituted by a heterocycle or $R_3$ and $R_4$ form together a saturated cycle; $R_5$ and $R_6$ are hydrogen, a hydrocarbon chain, a phenyl or benzyl radical or $R_5$ and $R_6$ form together a saturated cycle; $R_7$ is hydrogen, a phenyl or benzyl radical, a group of the formula $CR_{12}(R_{13})C(O)OR_{14}$ or $OCR_{12}(R_{13})$ $OC(O)R_{14}$ or $OCR_{12}(R_{13})OC(O)OR_{14}$. The disclosure also relates to the use of these compounds as a drug, and to a pharmaceutical composition containing said compounds and a pharmaceutically acceptable carrier. The disclosure further relates to the combined use of at least one cannabinoid derivative and/or morphine or one derivative thereof and/or Gaba derivatives for enhancing the analgesic and anti-depressive effect of the compounds of the formula (I).

19 Claims, 3 Drawing Sheets

OTHER PUBLICATIONS

Noble, et al: "Protection of Endogenous Enkephalin Catabolism as Natural Approach to Novel Analgesic and Antidepressant Drugs"; Expert Opinion, Ther. Targets (2007) 11(2): 145-149.

Milne, et al: "Quaternay Naloxone Blocks Morhphine Analgesia in Spinal But Not Intact Rats"; Neuroscience Letters, 114 (1990), pp. 259-264.

Menendez, et al: "Initial Thermal Heat Hypoalgesia and Delayed Hyperalgesia in a Mujrine Model of Bone Cancer Pain", Science Direct, Brain Research 969 (2003), pp. 102-109.

Hargreaves, et al: "A New and Sensitive Method for Measuring Thermal Nociception in Cutaneous Hyperalgesia", Pain, 32 (1988), pp. 77-88.

Jutkiewicz, et al: "Behavioral and Neurobiological Effects of the Enkephalinase Inhibitor RB101 Relative to Its Antidepressant Effects", Science Direct, European Journal of Pharmacology 531 (2006), pp. 151-159.

Noble, et al: "Inhibition of the Enkephalin-Metabolizing Enzymes by the First Systemically Active Mixed Inhibitor Prodrug RB 101 Induces Potent Analgesic Responses in Mice and Rats", The Journal of Pharmacology and Experimental Therapeutics, vol. 261, No. 1, (1992), pp. 181-190.

Chen, et al: "Long Lasting Antinociceptive PRoperties of Enkephalin Degrading Enzyme (NEP and APN) Inhibitor Prodrugs", J. Med. Chem. 2001, 44, (2001), pp. 3523-3530.

Chen, et al: "Phoshinic Derivatives as New Dual Enkephalin-Degrading Enzyme Inhibitors: Synthesis, Biological Properties, and Antinociceptive Activities", J. Med. Chem. 43, (2000), pp. 1398-1408.

Hunskaar, et al: "Formalin Test in Mice, a Useful Technique for Evaluating Mild Analgesics", Journal of Neuroscience Methods, 14 (1985), pp. 69-76.

Schmidt, et al: "Analgesic Responses Elicited by Endogenous Enkephalins (protected by mixed peptidase inhibitors) in a Variety of Morphine-Sensitive Noxious Tests", European Journal of Pharmacology, 192 (1991), pp. 253-262.

Maldonado, et al: "Comparison of Selective and Complete Inhibitors of Enkephalin-Degrading Enzymes on Morphine Withdrawal Syndrome", European Journal of Pharmacology, 165 (1989), pp. 199-207.

Fournie-Zaluski, et al: "Analgesic Effects of Kelatorphan, a New Highly POtent Inhibitor of Multiple Enkephalin Degrading Enzymes", European Journal of Pharmacology, 102 (1984), pp. 525-528.

Desmeules, et al: "Selective Opioid Receptor Agonists Modulate Mechanical Allodynia in an Animal Model of Neuropathic Pain", Pain 53 (1993), pp. 277-285.

Coudore-Civiale, et al: "Enhancement of the Effects of a Complete Inhibitor of Enkephalin-Catabolzing Enzymes, RB 101, by a Cholecystokinin-B receptor antagonist in Diabetic Rats", British Journal of Pharmacology (2001) 133, pp. 179-185.

Kayser, et al: "Potent Antinociceptive Effects of Keltatorphan (a highly efficient inhibitor of multiple enkephalin-degrading enzymes) Systemically Administered in Normal and Arthritic Rats", Brain Research, 497 (1989), pp. 94-101.

Bennett, et al: "A Peripheral Mononeuropathy in Rat that Produces Disorders of Pain Sensation like those Seen in Man", Pain 33 (1988), pp. 87-107.

Baamonde, et al: "Antidepressant-Type Effects of Endogenous Enkephalins Protected by Systemic RB 101 are Mediated by Opioid $\delta$ and Dopamine D1 Receptor Stimulation", European Journal of Pharmacology, 216 (1992), pp. 157-166.

Authier, et al: "A New Animal Model of Vincristine-Induced Nociceptive Peripheral Neuropathy", NeuroToxicology 24 (2003), pp. 797-805.

Malmberg, et al: "Partial Sciatic Nerve Injury in the Mouse as a Model of Neuropathic Pain: Behavioral and Neuroanatomical Correlates", Pain 76 (1998), pp. 215-222.

Alexander, Jose et al.; "(Acyloxy)alkyl Carbamates as Novel Bioreversible Prodrugs for Amines: Increased Permeation Through Biological Membranes;" XP 000651965, J. Med. Chem, vol. 31, No. 2, 1988; pp. 318-322.

* cited by examiner 2A   2B

AMINO ACID DERIVATIVES, METHOD FOR PREPARING SAME, AND THERAPEUTIC USE THEREOF

CROSS-REFERENCE TO RELATED APPLICATIONS

This application is a National Phase Entry of International Application No. PCT/EP2009/055787, filed on May 13, 2009, which claims priority to French Application 0853092, filed on May 13, 2008, both of which are incorporated by reference herein.

BACKGROUND AND SUMMARY

The invention relates to novel mixed inhibitors of neprilysine and aminopeptidase N with prolonged action.

It is known that enkephalins -Tyr-Gly-Gly-Phe-Met and Tyr-Gly-Gly-Phe-Leu- are endogenous ligands of the μ and δ opioid receptors, the localizations of which (Waksman et al. (1985) Proc. Natl. Acad. Sci. USA, 83, 1523-1527) and the functions of which are different: the μ receptors are essentially involved in the transmission of nociceptive impulses and the δ receptors in the regulation of mood and adaptation behaviors, in particular to stress (as reviewed in Noble et Roques, 2007, Expert Opin. Ther. Targets, 11, 145-159), (Jutkiewicz et al., 2006, Eur. J. Pharmacol., 531, 151-159). Intracerebroventricular administration of exogenous enkephalins induces a transient analgesic response because of the very rapid catabolism of these peptides by two enzymes, neprilysine (NEP, E.C. 3.4.24.11) which cleaves the $Gly^3$-$Phe^4$ bond of enkephalins and aminopeptase N (APN, E.C. 3.4.11.2) which releases N-terminal tyrosine (as reviewed in Roques et al., 1993, Pharmacol. Rev. 45, 88-146).

Mixed inhibitors of these two enzymes are known which, by completely protecting the endogenous enkephalins from their enzymatic degradation, reveal the pharmacological, in particular analgesic and antidepressive activities of enkephalins. The mixed inhibitors of both of these enzymatic activities, as described in the prior art, are compounds with a hydroxamate function (FR 2 518 088 and FR 2 605 004), aminophosphine compounds (FR 2 755 135 and FR 2 777 780) and aminoacid derivatives (FR 2 651 229 and WO2007/048787). In the case of compounds with a hydroxamate function, good activity in vitro and in vivo after administration via an intracerebroventricular route was observed (Eur. J. Pharmacol. 102, (1984), 525-528; Eur. J. Pharmacol., 165, (1989), 199-207; Eur. J. Pharmacol., 192, (1991), 253-262); significant activity was also able to be demonstrated after intravenous administration (iv) in an arthritic rat model (Brain Research, 497, (1989), 94-101). In the case of phosphine derivatives and aminoacid derivatives described in the application FR 2 651 229, good activity in vivo was demonstrated after administration via an iv route, when the investigated molecules were solubilized in a mixture of oil, ethanol and water (J. Med. Chem., 43, (2000), 1398-1408; J. Med. Chem., 44, (2001), 3523-3530; J. Pharm. Exp. Ther., 261, (1992), 181-190). The aminoacid derivatives described in the application WO2007/048787 are mixed inhibitors soluble in an aqueous medium, which have analgesic properties after administration via an iv route and via an oral route into laboratory animals, at doses compatible with administration into humans. Unfortunately, these molecules in animal pain models have a short action period (about 40 min) with a maximum around 10 min. and return to normal conditions after 15-30 min, which may represent a significant handicap for therapeutic uses, if the action period was of the same order in humans.

It will be recalled that the action period is the time during which, at its action site, the active ingredient contained in the drug produces its therapeutic or preventive effect. It is then eliminated by the organism. With the purpose of improving the action period of these molecules, modifications in their structures were made.

One of the objects of the invention is to provide novel water-soluble compounds capable of inhibiting together both enzymatic activities responsible for the degradation of enkephalins and of expressing their pharmacological properties on central and peripheral tests after administration, notably via an iv route or via an oral route, and for which the action period on the laboratory animal is equal to or longer than 120 min. Consequently, the novel compounds have properties of morphine substances, in particular analgesia, beneficial effects on behavior (decrease in the emotional component of pain and in antidepressive responses) and peripheral (antidiarrheic, antitussive, anti-inflammatory) effects without having the major drawbacks thereof (tolerance, physical and psychic addictions, respiratory depression, constipation, nausea, etc. ... ).

Further, inflammatory, neurogenic and neuropathic pains, for which the peripheral component is significant, and nociceptive pains are reduced or even eliminated by the compounds of the invention notably administered via an oral route, and this without the latter being forced to attain the central nervous system. This very interesting but unexpected result was formerly demonstrated by the use of an antagonist—methylaloxonium—incapable of entering the brain (Milne R. J. et al. (1990) Neuroscience Lett. 114, 259-264). This totally reduces all the effects due to the stimulation of cerebral opioid receptors by the compounds of the invention, without altering the analgesic effects of the compounds on these pains, in particular on neurogenic, neuropathic, neuroinflammatory and nociceptive pains.

Another object of the invention is to propose combinations between known compounds for their antinociceptive properties but having harmful secondary effects at strong doses, and the compounds claimed in the present invention. These combinations more particularly relate to morphine and its derivatives, $\Delta^9$-tetrahydrocannabinol ($\Delta^9$ THC) and its derivatives as well as derivatives of Gaba such as gabapentin or pregabalin. Indeed, strong potentialization of the antinociceptive responses obtained by combination of subactive doses of one of the compounds claimed in the present application and of one of the aforementioned analgesics (morphine, ($\Delta^9$ THC, gabapentin) was able to be ascertained.

The object of the invention is more particularly compounds having the following formula (I):

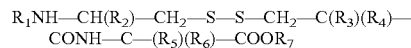

wherein:

$R_1$ represents an (acyloxy)alkyl carbamate group

—(CO)—O—$C(R_8)(R_9)$—OC(O)—$R_{10}$, wherein $R_8$ and $R_9$ independently of each other represent a hydrogen atom, an alkyl, aryl, arylakyl, cycloalkyl, cycloheteroalkyl, heteroalkyl, heteroaryl or heteroarylalkyl group; or taken together, $R_8$ and $R_9$ may form a cycloalkyl with 5 or 6 members;

$R_{10}$ represents an alkyl, aryl, arylalkyl, cycloalkyl, cycloheteroalkyl, heteroalkyl, heteroaryl or heteroarylalkyl group;

$R_2$ represents:
- a linear or branched saturated hydrocarbon chain having 1 to 6 carbon atoms, optionally substituted with:
  - an OH, $OR_{11}$, SH, $SR_{11}$ or $S(O)R_{11}$ radical, in each of these radicals, $R_{11}$ represents a linear or branched hydrocarbon chain with 1 to 4 carbon atoms, a phenyl radical or a benzyl radical,
- a phenyl or benzyl radical, optionally substituted with:
  - 1 to 5 halogen atoms, notably fluorine,
  - an OH, $OR_{11}$, SH, $SR_{11}$ or $S(O)R_{11}$ radical, $R_{11}$ having the same meaning as earlier,
  - a methylene radical substituted with a 5 or 6 members, aromatic or saturated, heterocycle, having as a heteroatom, a nitrogen or sulfur atom, optionally oxidized as an N-oxide or S-oxide, when $R_4$ represents a hydrogen atom, $R_3$ represents:
- a phenyl or benzyl radical optionally substituted with:
  - 1 to 5 halogen atoms;
  - an $SR_{11}$, $S(O)R_{11}$ or $OR_{11}$ radical, $R_{11}$ having the same meaning as earlier;
  - an amino group optionally mono- or di-substituted with a cyclic or linear aliphatic group having 1 to 6 carbon atoms;
- a heteroaryl with 5 or 6 members, the heteroatom being an oxygen, a sulfur or nitrogen atom;
- a methylene group substituted with a 5 or 6 members, aromatic or saturated, heterocycle, the heteroatom being an oxygen, nitrogen or sulfur atom, the nitrogen and sulfur atoms may be oxidized as an N-oxide or S-oxide;

when $R_4$ is different from H, $R_3$ and $R_4$ taken together form a saturated cycle with 5 or 6 members;

$R_5$ and $R_6$ independently of each other represent:
- a hydrogen atom,
- a linear or branched saturated hydrocarbon chain, having from 1 to 6 carbon atoms, optionally substituted with an OH, $OR_{11}$, SH or $SR_{11}$, COOH or $COOR_{11}$ radical, in each of these radicals, $R_{11}$ has the same meaning as earlier,
- a phenyl or benzyl radical, optionally substituted with:
  - a linear or branched alkyl chain having 1 to 4 carbon atoms;
  - 1 to 5 halogens, notably fluorine or bromine;
  - an OH, $OR_{11}$, SH or $SR_{11}$ radical, $R_{11}$ having the definition as earlier;

or taken together $R_5$ and $R_6$ from a saturated cycle with 5 or 6 members;

$R_7$ represents
- a hydrogen atom;
- a phenyl or benzyl radical optionally substituted with 1 to 5 halogens, notably fluorine;
- a group of formula $CR_{12}(R_{13})C(O)OR_{14}$;
- a group $CR_{12}(R_{13})OC(O)R_{14}$;
- a group $CR_{12}(R_{13})OC(O)OR_{14}$;

$R_{12}$ and $R_{13}$ independently of each other represent a hydrogen atom, an alkyl, aryl, arylalkyl, cycloalkyl, cycloheteroalkyl, heteroalkyl, heteroaryl or heteroarylalkyl group;
taken together $R_{12}$ and $R_{13}$ may form a cycloalkyl with 5 or 6 members.

$R_{14}$ represents an alkyl, aryl, arylalkyl, cycloalkyl, cycloheteroalkyl, heteroalkyl, heteroaryl or heteroarylalkyl group; as well as the addition salts of said compound (I) with pharmaceutically acceptable mineral or organic bases and each of its isomers, in particular its optical isomers (enantiomers and diastereoisomers).

For the "drug" portion of the molecule, i.e. the formula portion—NH—C*H($R_2$)—$CH_2$—S—S—$CH_2$—C*($R_3$)($R_4$)—CONH—C*($R_5$)($R_6$)—COO— the compounds according to the invention potentially have at most 3 asymmetric carbons, indicated by an asterisk, and which is reduced to a single centre of asymmetry when ($R_3$)($R_4$) and ($R_5$)($R_6$) form rings without any asymmetry. These centers are optically pure, with an absolute configuration like that of a natural aminoacid, i.e. an S configuration. The possible centers of asymmetry of the "prodrug" portions, i.e. for the substituents $R_1$ and $R_7$, are not resolved: these potential centers of symmetries may therefore be equally of R or S configuration.

The object of the invention is also addition salts of the compounds of formula (I), obtained with pharmacologically acceptable organic or mineral bases. In the present invention, "pharmaceutically acceptable" is meant to refer to what is useful in the preparation of a pharmaceutical composition, which is generally secure, non-toxic and neither biologically nor otherwise undesirable and which is acceptable for veterinary use as well as for human pharmaceutical use.

Further, "pharmaceutically acceptable salts" of a compound, are meant to refer to salts which have the desired pharmacological activity of the parent compound. Such salts comprise the salts formed when an acid proton present in the parent compound is either replaced with a metal ion, for example an alkaline metal ion, an earth alkaline metal ion; or coordinates with an organic or inorganic base. The acceptable organic bases comprise diethanolamine, ethanolamine, N-methylglucamine, triethanolamine, tromethamine, and the like, or natural basic aminoacids (for example lysine, arginine, alanine, asparagine, aspartic acid, cysteine, glutamine, glutamic acid, glycine, histidine, isoleucine, leucine, methionine, phenylalanine, proline, serine, threonine, tryptophan, tyrosine and valine) or non-natural basic aminoacids (such as pseudo-lysine). The acceptable inorganic bases in particular comprise aluminium hydroxide, calcium hydroxide, potassium hydroxide, lithium hydroxide, sodium carbonate and sodium hydroxide. Advantageously, the acid proton is displaced by a $Na^+$ ion, notably by using sodium hydroxide.

Within the scope of the present invention, the expression "hydrocarbon chain" refers to linear or branched alkanes, alkenes, or alkynes. In particular, the expression "saturated hydrocarbon chain" refers to either linear or branched alkyl radicals including from 1 to 6 carbon atoms ($C_1$-$C_6$) or from 1 to 4 carbon atoms ($C_1$-$C_4$). As an example of alkyl radicals including 1 to 4 carbon atoms, mention may be made of methyl, ethyl, propyl, butyl, isopropyl, 1-methyl-ethyl, 1-methyl-propyl, 2-methyl-propyl radicals. As an example of alkyl radicals including from 1 to 6 carbon atoms, mention may further be made of pentyl, hexyl, 1-methyl-butyl, 1-methyl-pentyl, 2-methyl-butyl, 2-methyl-pentyl, 3-methyl-butyl, 3-methyl-pentyl, 4-methyl-pentyl or 1-ethyl-propyl, or 1-ethyl-butyl, 2-ethyl-butyl radicals.

The expression "unsaturated hydrocarbon chain" refers to linear or branched, alkenyl radicals (at least one double bond), for example vinyl, allyl radicals or the like, or alkenyl radicals (at least one triple bond) including from 2 to 6 carbon atoms, or from 2 to 4 carbon atoms. By the term "heteroalkyl", is meant in the sense of the present invention, any hydrocarbon chain, as defined earlier, containing one or several heteroatoms, such as for example sulfur, nitrogen or oxygen atoms. By the term "cycloalkyl", is meant in the sense of the present invention, any hydrocarbon ring, either saturated or not, but non-aromatic, with 3 to 7 members, in particular 5 or 6 members, such as cyclopentyl and cyclohexyl.

By the term "cycloheteroalkyl", is meant in the sense of the present invention, any hydrocarbon ring, either saturated or not, but non-aromatic, with 5 to 7 members, containing one or more heteroatoms, such as for example sulfur, nitrogen or oxygen atoms. By the expression "aliphatic, cyclic or linear group", is meant a "hydrocarbon chain" or a "cycloalkyl" as defined earlier. By the term "aryl", is meant in the sense of the present invention, one or more aromatic rings having from 5 to 10 carbon atoms, which may be fused with each other. In particular, aryl groups may be monocyclic or bicyclic groups such as for example the phenyl or naphthyl group. Advantageously, the aryl group is a phenyl.

By the term "heteroaryl", is meant in the sense of the present invention, any aromatic group comprising from 5 to 10 cyclic atoms, which are carbon atoms or one or more heteroatoms, such as for example sulfur, nitrogen or oxygen atoms. The heteroaryl according to the present invention may be formed by one or two fused rings. Examples of heteroaryl groups are quinolyl, isoquinolyl, imidazolyl, indolyl, pyridyl, triazinyl, thiazoyl, and thiophenyl groups.

The term "aralkyl" within the scope of the present invention, designates aryl radicals (as defined earlier) bound to alkyl radicals (as defined earlier) such as for example benzyl or phenethyl. The term "heteroaralkyl" within the scope of the present invention, refers to heteroaryl radicals (as defined earlier) bound to alkyl radicals (as defined earlier). By the term "heterocycle", is meant a "cycloheteroalkyl" or a "heteroaryl" as defined earlier. As an example of aromatic or saturated heterocyclic rings with 5 or 6 atoms, having as a heteroatom a nitrogen or sulfur atom, mention may be made, but without any limitation, of the following radicals: thienyl, pyrrolyl, imidazolyl, pyrazolyl, isothiazolyl, pyridyl, pyrazinyl, pyrimidinyl, pyridazinyl, pyrrolidinyl, pyrrolinyl, imidazolidinyl, pyrazolidinyl, pyrazolinyl, piperidyl, piperazinyl, thiadiazolyl, the nitrogen and sulfur atoms being optionally oxidized as an N-oxide or S-oxide. As an example of aromatic or saturated heterocyclic rings with 5 or 6 atoms, having as a heteroatom an oxygen atoms, mention may be made, but without any limitation, of the following radicals: furyl, pyranyl, isoxazolyl, morpholinyl, furazanyl, oxazolyl, oxazolidinyl, oxazolinyl. The term "halogen" used here refers to a chlorine, bromine, iodine and fluorine atom.

The radical $R_1$ advantageously represents an (acyloxy) alkyl carbamate group

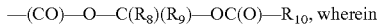
—(CO)—O—C($R_8$)($R_9$)—OC(O)—$R_{10}$, wherein $R_8$ and $R_9$ independently of each other represent a hydrogen atom or an alkyl group; and $R_{10}$ represents an alkyl group, in particular an isopropyl.

The radical $R_2$ advantageously represents an alkyl radical having from 1 to 4 carbon atoms, optionally substituted with an $OR_{11}$, $SR_{11}$ or $S(O)R_{11}$ radical, in each of these radicals, $R_{11}$ has the same meaning as earlier. $R_2$ still more advantageously represents an alkyl radical having from 1 to 4 carbon atoms substituted with an $SR_{11}$ or $S(O)R_{11}$ radical $R_{11}$ having the same meaning as earlier, in particular $R_{11}$ represents a linear or branched saturated hydrocarbon chain with 1 to 4 carbon atoms and more advantageously a methyl group.

According to an advantageous alternative of the invention, the radical $R_4$ represents a hydrogen atom. Within the scope of this alternative, the radical $R_3$ advantageously represents:
  a benzyl or phenyl radical,
  a methylene radical substituted with an aromatic or saturated heterocycle with 5 or 6 atoms, having as a heteroatom a nitrogen or sulfur atom, optionally oxidized as an N-oxide or S-oxide.
In particular the radical $R_4$ represents a hydrogen atom and the radical $R_3$ represents a benzyl radical or a methylene radical substituted with an aromatic or saturated heterocycle with 5 or 6 atoms, having as a heteroatom, a nitrogen or sulfur atom, optionally oxidized as an N-oxide or S-oxide, even more advantageously a benzyl radical.

According to another advantageous alternative of the invention, the radicals $R_4$ and $R_3$ form together with the carbon which bears them a cycloalkyl with 5 or 6 members, in particular a cyclopentane or a cyclohexane. The radical $R_5$ advantageously represents a hydrogen atom. The radical $R_6$ advantageously represents a hydrogen atom or an alkyl radical having from 1 to 6 carbon atoms, even more advantageously 1 to 4 carbon atoms, optionally substituted with an OH, $OR_{11}$, SH, or $SR_{11}$, COOH or $COOR_{11}$ radical, in each of these radicals, $R_{11}$ has the same meaning as earlier. The radical $R_6$ still more advantageously represents a hydrogen atom or an alkyl radical having from 1 to 6 carbon atoms, sill more advantageously 1 to 4 carbon atoms, substituted with an OH, SH, COOH or $COOR_{11}$ radical, $R_{11}$ having the same meaning as earlier.

The radical $R_7$ advantageously represents:
  a hydrogen atom;
  a phenyl or benzyl radical;
  an alkyl radical having from 1 to 4 carbon atoms;
  a $CR_{12}(R_{13})O(CO)OR_{14}$ group, wherein $R_{12}$, $R_{13}$ and $R_{14}$ have the same meaning as earlier, in particular $R_{12}$ represents a hydrogen atom and $R_{13}$ and $R_{14}$ independently of each other represent a $C_1$-$C_4$ alkyl group optionally substituted with a methoxy group or a $C_5$-$C_6$ cycloalkyl group.
In particular, the radical $R_7$ represents a hydrogen atom or a benzyl radical.

The invention in particular relates to the following compounds:
1-(1-{2-[(1-ethoxycarbonyloxy-ethoxy carbonylmethyl)-carbamoyl]-3-phenyl-propyldisulfanylmethyl}-3-methylsulfanyl-propylcarbamoyloxy)-ethyl isobutyric acid ester.
1-{1-[2-(benzyloxycarbonylmethyl-carbamoyl)-3-phenyl-propyl-disulfanylmethyl]-3-methylsulfanyl-propylcarbamoyloxy}-ethyl isobutyric acid ester.
1-{1-[2-(carboxymethyl-carbamoyl)-3-phenyl-propyldisulfanyl-methyl]-3-methylsulfanyl-propylcarbamoyloxy}-ethyl isobutyric acid ester.
1-(1-{2-[(1-ethoxycarbonyloxy-ethoxycarbonylmethyl)-carbamoyl]-3-phenyl-propyldisulfanylmethyl}-3-methane-sulfinyl-propylcarbamoloxy)-ethyl isobutyric acid ester.
1-{1-[2-benzyloxycarbonylmethyl-carbamoyl)-3-phenyl-propyl-disulfanylmethyl]-3-methanesulfinyl-propylcarbamoyloxy}-ethyl isobutyric acid ester.
1-{1-2[2-(carboxymethyl-carbamoyl)-3-phenyl-propyl-disulfanylmethyl]-3-methanesulfinyl-propylcarbamoyloxy}-ethyl isobutyric acid ester.
2-({1-[2-(1-isobutyryloxy-ethoxycarbonylamino)-4-methylsulfinyl-butyldisulfanylmethyl]-cyclopentanecarbonyl}-amino)-succinic acid.
2-({1-[2-(1-isobutyryloxy-ethoxycarbonylamino)-4-methylsulfanyl-butyldisulfanylmethyl]-cyclopentanecarbonyl}-amino)-succinic acid.
Benzyl 2-({1-[2-(1-isobutyryloxy-ethoxycarbonylamino)-4-methanesulfinyl-butyldisulfanylmethyl]-cyclopentanecarbonyl}-amino)-succinic acid ester
Benzyl 2-({1-[2-(1-isobutyryloxy-ethoxycarbonylamino)-4-methylsulfanyl-butyldisulfanylmethyl]-cyclopentanecarbonyl}-amino)-succinic acid.

According to an advantageous alternative of the invention, the following compounds are preferred:
1-{1-[2-(carboxymethyl-carbamoyl)-3-phenyl-propyldisulfanyl-methyl]-3-methylsulfanyl-propylcarbamoyloxy}-ethyl isobutyric acid ester.

1-{1-[2-benzyloxycarbonylmethyl-carbamoyl)-3-phenyl-propyl-disulfanylmethyl]-3-methanesulfinyl-propylcarbamoyloxy}-ethyl isobutyric acid ester.

1-{1-2[2-(carboxymethyl-carbamoyl)-3-phenyl-propyl-disulfanylmethyl]-3-methanesulfinyl-propylcarbamoyloxy}-ethyl isobutyric acid ester.

2-({1-[2-(1-isobutyryloxy-ethoxycarbonylamino)-4-methane-sulfinyl-butyldisulfanylmethyl]-cyclopentanecarbonyl}-amino)-succinic acid.

2-({1-[2-(1-isobutyryloxy-ethoxycarbonylamino)-4-methylsulfanyl-butyldisulfanylmethyl]-cyclopentanecarbonyl}-amino)-succinic acid.

Benzyl 2-({1-[2-(1-isobutyryloxy-ethoxycarbonylamino)-4-methanesulfinyl-butyldisulfanylmethyl]-cyclopentanecarbonyl}-amino)-succinic acid ester.

Benzyl 2-({1-[2-(1-isobutyryloxy-ethoxycarbonylamino)-4-methylsulfanyl-butyldisulfanylmethyl]-cyclopentanecarbonyl}-amino)-succinic acid ester.

The compounds of formulae (I) are obtained:

by condensation of a β-aminothiol protected on the amine function by a ter-butyloxycarbonyl group (Boc) (II) with a mercaptoalkanoic acid (III) by means of methoxycarbonyl-sulfenyl chloride.

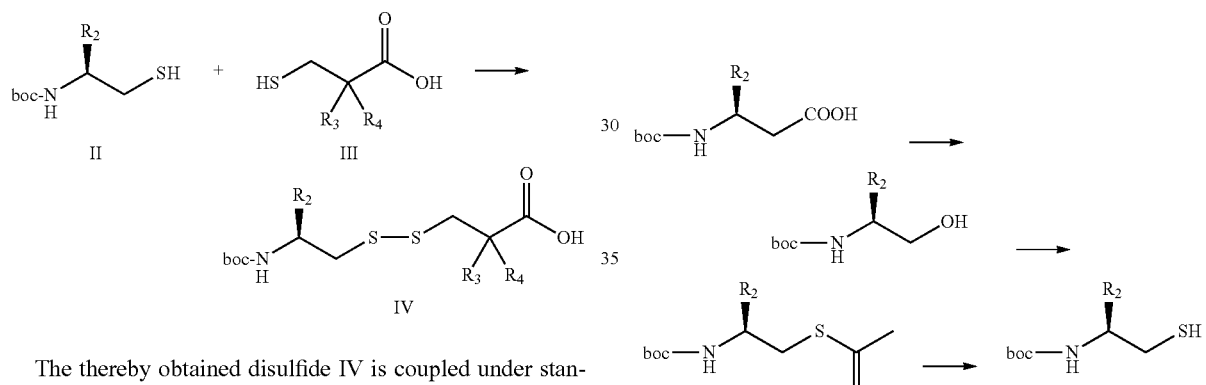

The thereby obtained disulfide IV is coupled under standard peptide coupling conditions, preferably by action of TBTU (O-(benzotriazol-1-yl)-N,N,N',N'-tetramethyluronium tetrafluoroborate) in the presence of DIEA (N,N-diisopropylethylamine), with an aminoester V, in order to lead to the compound VI.

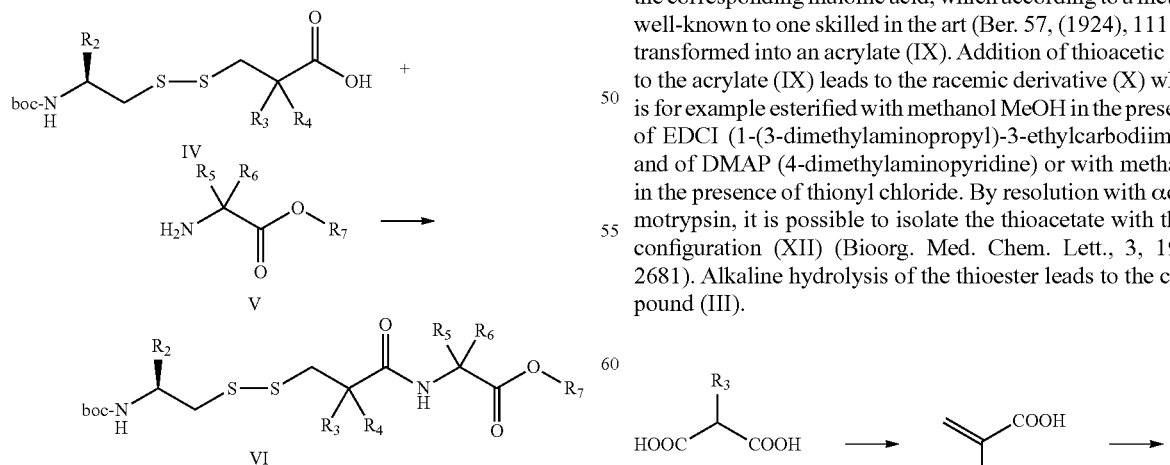

Deprotection of the Boc group of the compound VI is carried out by action of formic acid and the thereby formed compound VII reacts on an activated ester of the carbamate VIII ($R_1$—O-(p.$NO_2$)Ph or $R_1$—O-succinimide) in order to lead to the compound of formula (I).

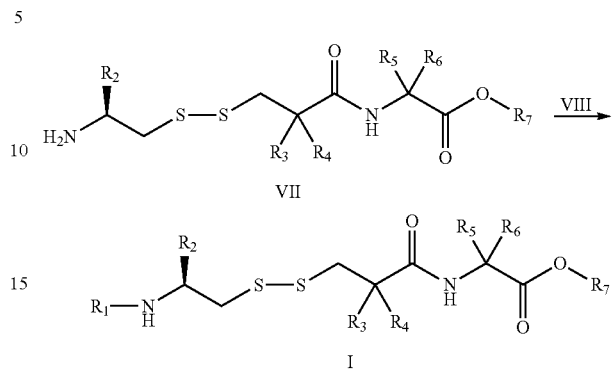

Boc-β-aminothiol (II) is obtained in three steps from the corresponding commercial Boc-α-amino-acid, of absolute S configuration, with configuration retention according to a method well-known to one skilled in the art (J. Med. Chem., 35, 1992, 1259).

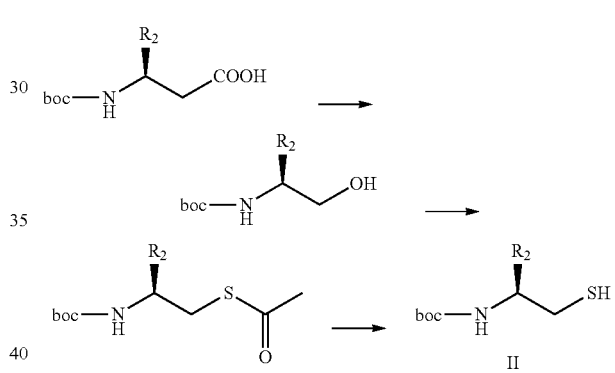

Two different methods are used for synthesizing the mercapto-alkanoic acid (III) depending on the nature of the $R_3$ and $R_4$ groups. If $R_4$=H, the compound (III) is obtained from the corresponding malonic acid, which according to a method well-known to one skilled in the art (Ber. 57, (1924), 1116) is transformed into an acrylate (IX). Addition of thioacetic acid to the acrylate (IX) leads to the racemic derivative (X) which is for example esterified with methanol MeOH in the presence of EDCI (1-(3-dimethylaminopropyl)-3-ethylcarbodiimide) and of DMAP (4-dimethylaminopyridine) or with methanol in the presence of thionyl chloride. By resolution with αchymotrypsin, it is possible to isolate the thioacetate with the S configuration (XII) (Bioorg. Med. Chem. Lett., 3, 1993, 2681). Alkaline hydrolysis of the thioester leads to the compound (III).

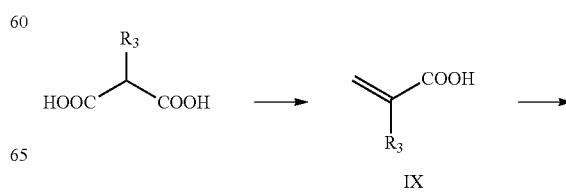

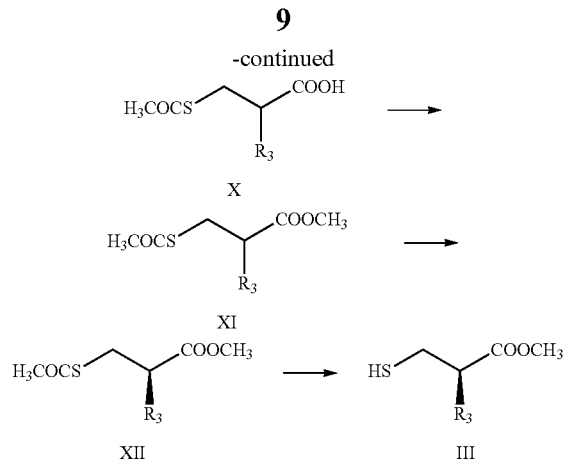

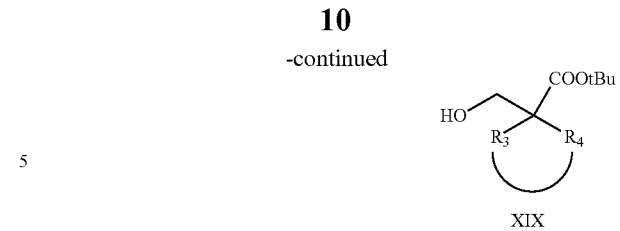

If $R_4 \neq H$, the compound (III) is obtained from the corresponding carboxylic acid (XIII). The latter, treated with ethyl chloroformate in the presence of LDA (lithium diisopropyl amide) in THF (tetrahydrofurane), leads to the compound (XIV). The carboxylic acid function of (XIV) is transformed into a mixed anhydride and is reduced by $NaBH_4$ into an alcohol (XV). Activation of the alcohol into a mesylate, and then substitution with potassium thioacetate leads to (XVI), which by alkaline hydrolysis gives (III).

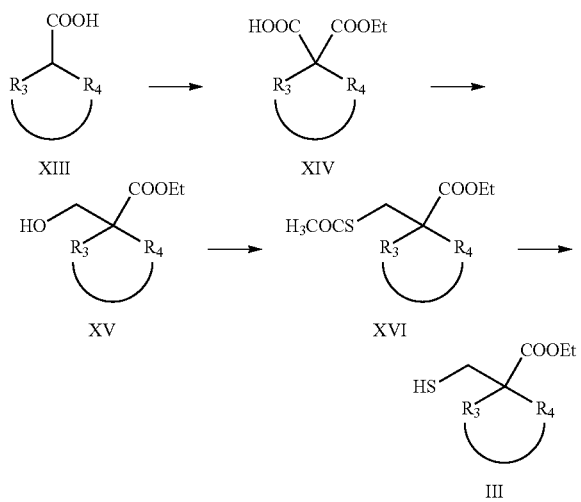

Another synthesis route for the compound III may be suggested from the acid XIII. The latter is transformed into a t-butyl ester XVII, and by treatment with LDA in THF followed by carbonatation with $CO_2$ leads to the derivative XVIII. The acid function of XVIII is then reduced into an alcohol in order to lead to the compound XIX. The sequence of reactions is identical with the one proposed in the preceding synthesis route.

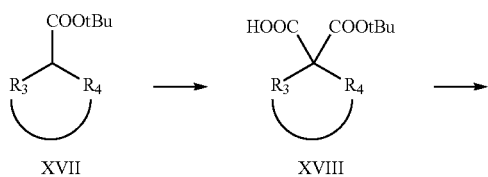

Another object of the invention is the use as a drug of the compounds as defined earlier or obtained by a method as defined earlier. The object of the invention is also the pharmaceutical compositions containing as an active ingredient at least one of the compounds of general formula (I) or one of its salts or hydrates of its salts in combination with one or more inert supports or other pharmaceutically acceptable carriers.

These compounds have the properties of morphine substances, in particular analgesia, and in particular in its peripheral components (inflammatory, neurogenic and neuropathic components), the beneficial effects on behavior, in particular in the case of depression and/or anxiety, without having the major drawbacks of the latter (tolerance, addiction, respiratory depression, constipation, etc. . . . ). Thus, against exogenous opioid agonists interacting with delta receptors, the mixed inhibitors according to the invention have antidepressive effects without causing any risk of triggering epileptiform fits or convulsions and act rapidly (Baamonde A. et al., 1992, Jutkiewicz E. M. et al., 2005). These compounds act on the periphery at the nociceptors (Stein C. et al. (1993) Lancet 342 321-324 (2003) Nature Med., 9, 119-124). Advantageously, the compounds according to the invention, administered orally, do not penetrate into the central nervous system in significant concentrations; this is confirmed by the observation that the pre-administration of an antagonist—methylnaloxonium—incapable of crossing the blood brain barrier blocks the analgesic action of the compounds according to the invention.

The main application of the compounds according to the invention is therefore in the field of analgesia, antidepressives and of the treatment of addictions. These compositions may in particular be used as a potent analgesic in neuroinflammatory, neurogenic, neuropathic and nociceptive pains, and as an anti-depressive agent. Further, the compounds according to the invention of formula (I) have after oral administration shown quite interesting effects on animal models predicting activities in humans, in:

various neuropathic pains, diabetic neuropathy, neuropathy triggered by pre-administration of an anti-cancer agent, of an anti-viral agent (HIV-1), by zoster, etc. . . . ;
hyperalgesia and allodynia: neurophatic and neuroinflammatory allodynia and hyperalgesia, pain caused by the administration of formalin, carrageenin, Freund's adjuvant, hyperalgesia and allodynia produced by partial and unilateral compression of the sciatic nerve, by administration of tumoral cells in the bone marrow, etc. . . . .

Analgesic drugs will refer to drugs which relieve or suppress pain without causing loss of sensations or of consciousness.

As a summary, the present invention aims at treating symptoms corresponding not only to pains by excess of nociceptive stimulations, but also neuropathic or neurogenic pains which no longer have a physiological role, for example in the form of a signal, but which have become really pathological and chronic. Among the neurophatic and neurogenic chronic pains potentially sensitive to the action of the compounds of formula (I), mention may be made as non-limiting examples, of the pains of peripheral or central neuropathies resulting from nerve lesions of traumatic origin (for example, brachial plexus), of metabolic origin (for example, diabetes, alcoholic neuropathy), infectious origin (for example, zoster, herpes), toxic origin (for example, arsenic, lead), invasive origin (cancer pain) or congenital origin, of radiculopathic (for example, dorsolumbar or cervical) origins, neuralgic (trigeminal nerve); pains of phantom limbs; non-inflammatory joint pains (for example, arthrosis); fibromyalgias; rachidian pains; postoperative pains; medicinal pains (for example, from antitumoral agents, antiviral agents). The compounds according to the invention may also be used in the treatment of multiple sclerosis, which is an inflammatory disease of the central nervous system. Very interestingly, the compounds according to the invention have a long period of action, in particular equal to or greater than 120 minutes, more advantageously equal to or greater than 150 minutes, still more advantageously equal to or greater than 180 minutes.

The pharmaceutical compositions according to the invention may, as an example, be compositions which may be administered via an oral, nasal (administration with an aerosol), sublingual (administration by perlingual diffusion), rectal, parenteral, intravenous, and percutaneous route. As an example of compositions which may be administered orally, mention may be made of tablets, gelatin capsules, granules, microspheres, powders and oral solutions or suspensions. Also very interestingly, the compounds according to the invention have proved to be particularly suitable for oral administration. This administration route thus allows action of the composition according to the invention without penetrating into the central nervous system. This is particularly interesting for suppressing all the undesired effects resulting from activation of the opioid receptors in the brain and/or the spinal cord. The same applies when the composition comprises complementary compounds, which may have undesired effects on the central nervous system such as for example natural cannabinoids or synthetic derivatives. This also allows an increase in the cerebral bioavailability of the components of the combinations.

According to an advantageous alternative of the invention, the compounds of formula (I) are used in combination with cannabinoids. In the sense of the present invention, the expression "cannabinoids" refers to $\Delta^9$, synthetic agonists of the CB1 receptor or inhibitors of degradation of anandamide. The cannabinoids introduced into the compositions according to the invention are preferably $\Delta^9$ THC.

The object of the invention is also the combination of the novel compounds according to the invention with morphine or one of its derivatives. The object of the invention is also more particularly the combination of the novel compounds according to the invention with derivatives of Gaba, such as gabapentin or pregabalin.

The object of the invention is also a pharmaceutical composition comprising at least one compound of formula (I) as defined earlier, at least:

one cannabinoid derivative, in particular $\Delta^9$ THC, or a protector of its metabolism (review Piomelli et al., TIPS, 2000), and/or morphine or one of its derivatives, and/or a derivative of Gaba, such as gabapentin or pregabalin and a pharmaceutically appropriate excipient, in particular an appropriate excipient for administration via an oral, nasal, intravenous or transcutaneous route.

The invention also relates to the use of at least one derivative of cannabinoids, in particular $\Delta^9$ THC, and/or morphine or one of its derivatives, and/or a derivative of Gaba, such as gabapentin or pregabalin, in a pharmaceutical composition in order to potentialize the analgesic and/or antidepressive effect of the compounds of formula (I) as defined earlier. The invention also relates to the use of a combination of at least one compound of formula (I) as defined earlier and of at least one derivative of cannabinoids, in particular $\Delta^9$ THC, and/or morphine, or one of its derivatives, and/or a derivative of Gaba, such as gabapentin or pregabalin, for preparing a drug intended for the treatment of depression and pain, in particular acute pain, inflammatory pain, neurogenic pain, neuropathic pain, psychogenic pain, allodynia.

Another object of the invention is a pharmaceutical composition comprising:

i) at least one compound of formula (I) as defined earlier
ii) at least one derivative of cannabinoids, and/or
iii) morphine or one of its derivatives, and/or
iv) at least one derivative of Gaba, such as gabapentin dr pregabalin, as combination products for simultaneous, separate use or spread out in time:

The effective dose of a compound of the invention varies according to many parameters, such as for example, the selected administration route, the weight, the age, the sex, the progression stage of the pathology to be treated and the sensitivity of the individual to be treated. Accordingly, the optimum dosage has to be determined, depending on parameters estimated to be relevant by the specialist in this field. The object of the invention is also a method for treating any of the diseases mentioned earlier, comprising the administration in a patient who requires such a treatment, of at least one of the compounds according to the invention or of a composition comprising at least one of these compounds. The compounds according to the invention may be used, in this method, either alone or combined notably with at least one of the compounds described earlier.

The invention will further be illustrated without being by any means limited by the examples hereafter. The list of the prepared compounds is given in Table I. For all of the compounds described in these examples 6, 8, 10, 12, 14, 16, 19 and 22.

$R_1$ represents the
—C(O)—O—CH(CH$_3$)—OC(O)-iPr radical.

$R_6$ represents a hydrogen atom.

TABLE 1

| | radicals of the examples | | | | |
|---|---|---|---|---|---|
| Example | $R_2$ | $R_3$ | $R_4$ | $R_5$ | $R_7$ |
| 6 | —CH$_2$—CH$_2$—S—CH$_3$ | BENZYL | H | H | —CH(CH$_3$)—OC(O)—O—C$_2$H$_5$ |
| 8 | —CH$_2$—CH$_2$—S—CH$_3$ | benzyl | H | H | benzyl |
| 10 | —CH$_2$—CH$_2$—S—CH$_3$ | benzyl | H | H | H |
| 12 | —CH$_2$—CH$_2$—SO—CH$_3$ | benzyl | H | H | —CH(CH$_3$)—OC(O)—O—C$_2$H$_5$ |
| 14 | —CH$_2$—CH$_2$—SO—CH$_3$ | benzyl | H | H | benzyl |
| 16 | —CH$_2$—CH$_2$—SO—CH$_3$ | benzyl | H | H | H |

TABLE 1-continued radicals of the examples

| Example | $R_2$ | $R_3$ | $R_4$ | $R_5$ | $R_7$ |
|---|---|---|---|---|---|
| 19 | —$CH_2$—$CH_2$—S—$CH_3$ | —$(CH_2)_4$— | | —$CH_2$—COOH | H |
| 22 | —$CH_2$—$CH_2$—SO—$CH_3$ | —$(CH_2)_4$— | | —$CH_2$—COOH | H |

DETAILED DESCRIPTION

Example 1

Synthesis of tert-butyl (1-mercaptomethyl-3-methyl-sulfanyl-propyl)-carbamic acid ester This compound is prepared following the procedure described in J. Med. Chem., 35, 1992, 2473. White solid; melting point 37° C.; Rf (cyclohexane (CHex)/ethyl acetate (AcOEt)) 1/1=0.73).

HPLC (Kromasil C18, $CH_3CN$ (0.1% TFA) 50%/$H_2O$ (0.1% TFA) 50%) Rt=15.7 min.

NMR ($CDCl_3$) δ (ppm) 1.30 (1H, t), 1.52 (9H, s), 1.80-1.90 (2H, m), 2.10 (3H, s), 2.55 (2H, t), 2.80 (2H, t), 3.88 (1H, m), 4.80 (1H, d).

Example 2

Synthesis of (2S)-2-benzyl-3-mercapto-propanoic acid

Step 1: Methyl 3-acetylsulfanyl-2-benzyl-propanoic acid ester, obtained by esterification of the corresponding acid, is treated with α-chymotrypsin according to the procedure described in Bioorg. Med. Chem. Lett., 3, (1993), 2681. Yield 71%; enantiomeric excess ee 88% $α_D^{20° C.}$–42.7°.

Step 2: (2S)-2-Benzyl-3-mercapto-propanoic acid

The compound of step 1 is dissolved in degassed methanol at 0° C. Under an inert atmosphere, 3 equivalents of NaOH (soda) 1N are added and the mixture is stirred for 30 min at room temperature. The mixture is acidified with HCl 6N and MeOH is evaporated under reduced pressure. The aqueous phase is extracted with EtOAc. The organic phase is washed with a saturated NaCl solution, dried on $Na_2SO_4$ and dry evaporated. A yellow oil is obtained. Quantitative yield.

HPLC (Kromasil Cl8 ($CH_3CN$ (0.1% TFA) 60%/$H_2O$ (0.1% TFA) 40%) Rt=4.96 min.

NMR ($CDCl_3$) δ (ppm) 1.5 (1H, t), 2.7-3.2 (5H, m), 7.25 (5H, m), 12 (1H, s).

Example 3

Synthesis of 2-(2-tert-butoxycarbonylamino-4-methylsulfanyl-butyldisulfanylmethyl)-3-phenyl-propanoic acid A mixture of 23 mL of MeOH and 23 mL of THF is cooled at 0° C. under nitrogen and chlorocarbonylsulfenyl chloride (1.3 mL, 1.1 equivalent) is added. The mixture is stirred for 15 min at 0° C. in order to obtain methoxycarbonylsulfenyl chloride. The compound of Example 1 (1.06 equivalent) in 16 mL of THF is added all at once. The mixture is brought down to room temperature and is stirred for 30 min. This solution is added dropwise to a solution of the compound of Example 2 (1 equivalent) in 100 mL of degassed $CHCl_3$ in the presence of $Et_3N$ (1 equivalent). The mixture is stirred for 1 hr at room temperature and the solvent is then dry evaporated. The residue is taken up in $CH_2Cl_2$ and the organic phase is washed with a 10% citric acid solution, a saturated NaCl solution, dried on $Na_2SO_4$. After filtration and dry evaporation, a pale yellow oil is obtained which is used as such for the subsequent reactions. Yield 98%

HPLC (Kromasil C18 ($CH_3CN$ (0.1% TFA) 70%/$H_2O$ (0.1% TFA) 30%) Rt=7.71 min.

NMR (DMSOd6) δ (ppm): 1.35 (9H, s), 1.7 (2H, m), 2.0 (3H, s), 2.4 (2H, t), 2.7-3.0 (5H, m), 3.70 (1H, s), 6.80 (1H, d), 7.20 (5H, m).

Example 4

Synthesis of 1-ethoxycarbonyloxy-ethyl amino-acetic acid ester trifluoroacetate

Boc-Gly (4.88 g) and $Et_3N$ (triethylamine) (4.65 mL, 1.2 equivalent) are dissolved in 25 mL of ethyl acetate. Ethyl-1-chloroethyl carbonate (prepared according to Barcelo et al., Synthesis, 1986, 627) (4.68 g, 1.1 equivalent) and NaI (1.64 g, 0.4 equivalents) are added and the mixture is refluxed for 16 hrs. The precipitate is filtered and 15 mL of ethyl acetate and 20 mL of water are added to the filtrate. The organic phase is separated and the aqueous phase is extracted three times with ethyl acetate. The collected organic phases are washed with a 10% citric acid solution, a 10% $NaHCO_3$ solution, a saturated NaCl solution, dried on $Na_2SO_4$, filtered and dry evaporated. An orange oil of 7.8 g is obtained. Yield 95%. Rf (cHexane/AcOEt: 8/2) 0.40.

The oily product of step 1 is put into solution in 24 mL of $CH_2Cl_2$ and 21.3 mL of TFA. After stirring for 1 h at room temperature, the reaction mixture is dry evaporated. The obtained yellow oil is taken up in a ether/hexane mixture. The formed precipitate is washed three times with the ether/hexane mixture and then is dried. White solid 7.2 g (Yield 85%)

NMR (DMSOd6) δ (ppm): 1.2 (3H, q), 1.5 (3H, d), 3.90 (2H, dd), 4.10 (2H, q), 6.75 (1H, q), 8.37 (3H, s).

Example 5

1-ethoxycarbonyloxy-ethyl[2-(2-tert-Butoxycarbonylamino-4-methylsulfanyl-butyldisulfanylmethyl)-3-phenyl-propionylamino]-acetic acid ester The compound of Example 3 (2 g), the compound of Example 4 (1.47 g, 1.1 equivalent), TBTU (1.62 g, 2 equivalents)- and DIEA (2.57 ml) are solubilized in 20 mL of DMF. The mixture is stirred for 15 min at room temperature, and the DMF is then evaporated under reduced pressure. The residue is taken up in ethyl acetate and the organic phase is washed with a 10% citric acid solution, a 10% $NaHCO_3$ solution and a saturated NaCl solution. The solution is dried on $Na_2SO_4$, filtered and dry evaporated. The raw product is purified on a silica column (cHexane/AcOEt: 6/4). White solid 2.06 g (Yield 75%)

HPLC Kromasil C18 (CH$_3$CN (0.1% TFA) 70%/H$_2$O (0.1% TFA) 30%) Rt=11.2 min. Mass (M+H)$^+$=631.

Example 6

1-(1-(2-[(1-ethoxycarbonyloxy-ethoxy-carbonyl methyl)-carbamoyl]-3-phenyl-propyldisulfanyl-methyl)-3-methyl sulfanyl-propylcarbamoyloxy)-ethyl isobutyric acid ester The compound of Example 5 (1.7 g) is solubilized in 17 mL of formic acid, and the mixture is stirred for 2 hrs at room temperature. The formic acid is evaporated in vacuo, the residue is taken up three times with cyclohexane and dry evaporated. Yellow oil 1.5 g (Yield 97%).

The obtained formate is solubilized in 20 mL of CH$_2$Cl$_2$ and 2.4 mL of DIEA (5 equivalents). 1.15 g (1.5 equivalent) of I-(2,5-dioxo-cyclopentyloxycarbonyloxy)-ethyl isobutyric acid ester is added and the mixture is stirred for 1 hr at room temperature. The solvent is evaporated and the residue is taken up with ethyl acetate. The organic phase is washed with water, with a 10% citric acid solution, a saturated NaCl solution, dried on Na$_2$SO$_4$ and then filtered and dry evaporated.

Purification by semipreparative HPLC on a Kromasil Cl8 column (CH$_3$CN (0.1% TFA)/H$_2$O (0.1% TFA): 70/30). White solid 0.96 g (Yield 50%)

HPLC (Kromasil C18 (CH$_3$CN (0.1% TFA)/H$_2$O (0.1% TFA): 70/30) Rt=10.98 min. Mass (M+H)$^+$=577

NMR (CDCl$_3$) δ (ppm): 1.10 (6H, d), 1.25 (3H, t), 1.5 (2×3H, d), 1.65-1.85 (2H, m) 2.47 (4H, m), 2.5 (1H, m), 2.5-3.00 (5H, m), 3.90-4.00 (3H, m), 4.15 (2H, q), 4.9 (1H, d), 6.4 (1H, t), 6.75 (2×IH, q), 7.20 (10H, m).

Example 7

Benzyl[2-(2-tert-butoxycarbonylamino-4-methylsulfanyl-butyldisulfanylmethyl)-3-phenyl-propionylamino]-acetic acid ester The compound of Example 3 (4 g) and glycine benzyl ester as a salt of APTS (4.55 g, 1.5 equivalent) are put into solution in DMF (20 mL). TBTU (3.43 g, 1.2 equivalent) and DIEA (5 mL) are added. The mixture is stirred for 15 min at room temperature. The reaction mixture is then treated according to the procedure described in Example 5. A white solid is obtained, 5.3 g (Yield 99%) Mass (M+H)=593.

HPLC (Kromasil C18, CH$_3$CN (0.1% TFA)/H$_2$O (0.1% TFA): 70/30) Rt=12.9 min NMR (CDCl$_3$) δ (ppm) 1.4 (9H, s), 1.7-1.9 (2H, m), 2.10 (3H, s), 2.5 (2H, m), 2.8-3.10 (7H, m), 3.80-4.10 (3H, m), 4.70 (1H, d), 5.15 (2H, s), 6.60 (1H, t), 7.20-7.40 (10H, m).

Example 8

1-{1-[2-(benzyloxycarbonylmethyl-carbamoyl)-3-phenyl-propyldisulfanylmethyl]-3-methylsulfanyl-propyl-carbamoyloxy}-ethyl isobutyric acid ester The compound of Example 7 (724 mg) is solubilized in 5 mL of TFA and 5 mL of CH$_2$Cl$_2$. The mixture is stirred for 3 hrs at 0° C. The reaction mixture is evaporated under reduced pressure and the residue is taken up with water and freeze-dried. White solid 720 mg (Yield 97%) Mass (M+H)$^+$607.

HPLC (Kromasil C18, (CH$_3$CN (0.1% TFA)/H$_2$O (0.1% TFA): 50/50) Rt=6.2 min

The obtained trifluoroacetate (720 mg) is solubilized in 10 mL of CH$_2$Cl$_2$. DIEA (1 mL, 5 equivalents) and then 500 mg (1.5 equivalent) of 1-(2,5-dioxo-cyclopentyloxycarbonyloxy)-ethyl isobutyric acid ester are added and the mixture is stirred for 1 hr at room temperature. The solvent is evaporated and the residue is taken up with ethyl acetate. The organic phase is washed with water, with a saturated NaCl solution and dried on Na$_2$SO$_4$. After filtration and dry evaporation, an oily compound is obtained which is purified by semipreparative HPLC on a Kromasil Cl8 column, CH$_3$CN (0.1% TFA/H$_2$O (0.1% TFA) 70/30. White solid 390 mg (Yield 48.5%). Mass (M+H)$^+$651.

HPLC Kromasil Cl8 (CH$_3$CN (0.1% TFA) 70%/H$_2$O (0.1% TFA) 30%) Rt=12.5 min.

NMR (CDCl$_3$) δ (ppm): 1.1 (6H, d), 1.5 (3H, d), 1.7-1.9 (2H, m), 2 (3H, s), 2.5 (3H, m), 2.7-3.0 (7H, m), 3.7-4.2 (3H, m), 4.95 (1H, d), 5.15 (2H, s), 6.4 (1H, t), 6.7 (1H, q), 7.2 (10H, m).

Example 9 tert-butyl[2-(2-tert-butoxycarbonylamino-4-methylsulfanyl-butyldisulfanylmethyl)-3-phenyl-propionylamino]-acetic acid ester The compound of Example 3 (1 g) and glycine tert-butyl ester (563 mg, 1.5 equivalent) are put into solution in 5 mL of DMF in the presence of TBTU (857 mg, 1.2 equivalent) and DIEA (1.24 mL). The mixture is stirred for 15 min at room temperature, and the reaction mixture is then treated as described in Example 5. A white solid is obtained 918 mg (Yield 74%).

HPLC Kromasil C18 (CH$_3$CN (0.1% TFA) 70%/H$_2$O (0.1% TFA) 30%) Rt=13.3 min. Mass (M+H)$^+$559

Example 10

1-{1-[2-(carboxymethyl-carbamoyl)-3-phenyl-propyl-disulfanylmethyl]-3-methylsulfanyl-propylcarbamoyl-oxy}-ethyl isobutyric acid ester The compound of Example 9 (914 mg) is solubilized in 5 mL of CH$_2$Cl$_2$ and 5 mL of TFA and the mixture is stirred at room temperature for 3 hrs. After dry evaporation, the residue is taken up with water and freeze-dried. White solid 844 mg (Quantitative yield). The trifluoroacetate (844 mg) is solubilized in 10 mL of CH$_2$Cl$_2$. 1.34 mL (5 equivalents) of DIEA and 670 mg (1.5 equivalent) of 1-(2,5-dioxo-cyclopentyloxylcarbonyloxy)-ethyl isobutyric acid ester are added and the mixture is stirred for 1 hr at room temperature. The reaction medium is then treated as described in Example 6. The raw product is purified by semipreparative HPLC on a Kromasil Cl8 column (CH$_3$CN (0.1% TFA/H$_2$O (0.1% TFA): 55/45. White solid 400 mg (Yield 44%).

HPLC Kromasil Cl8 (CH$_3$CN (0.1% TFA) 60%/H$_2$O (0.1% TFA) 40%) Rt=7.80 min Mass (M+H)$^+$561.

NMR (CDCl$_3$) δ (ppm): 1.0 (6H, dd), 1.4 (3H, dd), 1.6-1.75 (2H, m), 2.0 (3H, s), 2.5 (3H, m), 2.8-3.1 (7H, m), 3.8-4.1 (3H, m), 5.0 (1H, d), 6.7 (1H, q), 7.2 (5H, m).

The sodium salt of the compound 10 is obtained by solubilizing the acid in acetonitrile and then by adding 1 equivalent of NaHCO$_3$ in solution in water. The thereby obtained solution is freeze-dried. White solid (Yield 96%)

Example 11

1-ethoxycarbonyloxy-ethyl [2-(2-tert-butoxycarbonyl-amino-4-methanesulfinyl-butyldisulfanyl-methyl)-3-phenyl-propionylamino]-acetic acid ester The compound of Example 5 (2 g) is solubilized in 40 mL of ethanol. 32 mL of a 0.2M NaIO$_4$ solution (2 equivalents) at 0° C. and the mixture is stirred for 3 hrs at 0° C. The precipitate is filtered and the filtrate is dry evaporated. The residue is taken up in ethyl acetate and the organic phase is washed with water, with a saturated NaCl solution, dried on Na$_2$SO$_4$. After filtration and evaporation, the raw product is purified by chromatography.

White solid 1.5 g (Yield 70%)

HPLC (Kromasil Cl8 (CH$_3$CN (0.1°)/0.1%. TFA) 60%/H$_2$O (0.1% TFA) 40%) Rt=8.3 min. Mass (M+H)$^+$=635

Example 12

1-(1-{2-[(1-ethoxycarbonyloxy-ethoxy-carbonylmethyl)-carbamoyl]-3-phenyl-propyldisulfanyl-methyl}-3-methanesulfinyl-propylcarbamoloxy)-ethyl isobutyric acid ester The compound of Example 11 (1.5 g) is solubilized in 20 mL of formic acid and the mixture is stirred for 1 hr at room temperature. The formic acid is evaporated in vacuo and the residue is taken up with water and freeze-dried.

White Solid 1.38 G.

The obtained formate (1.38 g) is solubilized in CH$_2$Cl$_2$ and the carbamate (1.5 equivalent) (1-(2,5-dioxo-cyclopentyloxycarbonyloxy)-ethyl isobutyric acid ester) and DIEA (3 equivalents) are added. The mixture is stirred for 1 hr at room temperature and the solvent is then evaporated under reduced pressure. The residue is taken up with ethyl acetate. The organic phase is washed with a 10% citric acid solution, a saturated NaCl solution, dried on Na$_2$SO$_4$, filtered and dry evaporated. The raw product is purified by HPLC on a Kromasil column (semipreparative CH$_3$CN (0.1% TFA)/H$_2$O (0.1% TFA): 50/50

Yield 54%.

HPLC Kromasil C18 (CH$_3$CN (0.1% TFA) 50%/H$_2$O (0.1% TFA) 50%) Rt=14.55 min. Mass (M+H)$^+$=693.

NMR (DMSOd6) δ (ppm): 1.0 (6H, dd), 1.15 (3H, t), 1.4 (2×3H, d), 1.65-1.90 (2H, m), 2.4-3.0 (13H, m), 3.75 (1H), 3.9 (2H, d), 4.0 (2H, q), 5.1 (2H, s), 6.65 (2H, m), 7.1-7.3 (5H, m), 7.5 (1H, d), 8.5 (1H, t).

Example 13

Benzyl[2-(2-tert-butoxycarbonylamino-4-methanesulfinyl-butyldisulfanyl-methyl)-3-phenyl-propionylamino]-acetic acid ester The compound of Example 7 (5.3 g) is treated under the conditions of Example 11 in order to lead to 5.19 g of the expected compound. Yield 95%

HPLC Kromasil Cl8 (CH$_3$CN (0.1% TFA) 60%/H$_2$O (0.1% TFA) 40%) Rt=7.3 min

Example 14

1-{1-[2-benzyloxycarbonylmethyl-carbamoyl)-3-phenyl-propyldisulfanylmethyl]-3-methanesulfinyl-propyl-carbamoyloxy}-ethyl isobutyric acid ester The compound of Example 13 (3.1 g) is treated with 50 mL of formic acid and the reaction is treated as described in Example 12. White solid 2.85 g (Yield 99%)

The obtained formate (1.41 g) is solubilized in a mixture of 20 mL of dioxane and 20 mL of water. 1.1 g (8 equivalents) of NaHCO$_3$ and 1.13 g (1.5 equivalents) of 1-(4-nitro-phenoxycarbonyloxy)-ethyl isobutyric acid ester are added and the mixture is stirred for 72 hrs at room temperature. The dioxane is dry evaporated and the aqueous phase is extracted with ethyl acetate. The organic phase is washed with a saturated NaCl solution, dried on Na$_2$SO$_4$. After filtration and dry evaporation, the product is purified by semipreparative HPLC on a Kromasil C18 column (CH$_3$CN (0.1% TFA)/H$_2$O (0.1% TFA): 55/45. White solid 1.0 g (Yield 59%)

HPLC Kromasil C18 (CH$_3$CN (0.1% TFA) 60%/H$_2$O (0.1% TFA) 40%) Rt=8.21 min. Mass (M+H)$^+$667

NMR (DMSOd6) δ (ppm): 1.0 (6H, dd), 1.4 (3H, d), 1.65-1.90 (2H, m), 2.4-3.0 (13H, m), 3.75 (1H), 3.9 (2H, d), 5.1 (2H, s), 6.65 (1H, m), 7.1-7.3 (10H, m), 7.5 (1H, d), 8.5 (1H, t).

Example 15 tert-butyl[2-(2-tert-butoxycarbonylamino-4-methanesulfinylmethyl)-3-phenyl-propionylamino]-acetic acid ester The compound of Example 9 (745 mg) is treated under the conditions of Example 11 in order to lead to 781 mg (quantitative yield) of the expected product.

HPLC Kromasil Cl8 (CH$_3$CN (0.1% TFA) 70%/H$_2$O (0.1% TFA) 30%) Rt=4.65 min.

NMR (DMSOd6) δ (ppm): 1.4 (18H, s), 1.7-1.9 (2H, m), 2.5-3 (12H, m), 3.7 (2H, d+1H, m), 6.9 (1H, d), 7.2 (5H, m), 8.4 (1H, t).

Example 16

1-{1-2[2-(carboxymethyl-carbamoyl)-3-phenyl-propyldisulfanyl-methyl]-3-methanesulfinyl-propyl-carbamoyl-oxy}-ethyl isobutyric acid ester The compound of Example 15 (760 mg) is treated with 5 mL of TFA in 5 mL of CH$_2$Cl$_2$ and the reaction is then stirred for 3 hrs at room temperature. The solvents are then evaporated under reduced pressure, the residue is taken up in water and freeze-dried. A white product is obtained (686 mg; Yield 99%).

The obtained compound (686 mg) is solubilized in 10 mL of water and 10 mL of dioxane. 572 mg (8 equivalents) of NaHCO$_3$ and 587 mg (1.5 equivalent) of (I-(4-nitro-phenoxycarbonyloxy)-ethyl isobutyric acid ester are added. The mixture is stirred for 12 hrs at room temperature. The dioxane is evaporated under reduced pressure and the aqueous phase is extracted with ethyl acetate. The organic phase is washed with a saturated NaCl solution, dried on Na$_2$SO$_4$, filtered and dry evaporated. The raw product is purified by semipreparative HPLC on a Kromasil Cl8 column (CH$_3$CN (0.1% TFA)/H$_2$O (0.1% TFA): 35/65. White solid 212 mg. Yield 28.1%)

HPLC Kromasil Cl8 (CH$_3$CN (0.1% TFA) 40%/H$_2$O (0.1% TFA) 60%) Rt=11.98 min. Mass (M+H)$^+$=577

NMR (DMSOd6) δ (ppm): 1.0 (2×3H, d), 1.4 (3H, d), 1.7-1.9 (2H, m), 2.5-3.0 (13H, m), 3.7 (2H, d=1H, m), 6.65 (1H, m), 7.2 (5H, m), 7.5 (1H, d), 8.4 (1H, t).

Example 17 tert-butyl cyclopentane-1,1-dicarboxylic acid ester

Tert-butyl cyclopentane-dicarboxylic acid ester (prepared according to J. Med. Chem., 1994, 37, 2461-2476) (10 g) is solubilized in 50 mL of THF under nitrogen. The LDA solution (1.3 equivalent) prepared from 10.71 mL of diisopropylamine and from 47.75 mL of butyllithium 1.6 M in hexane under nitrogen are added at −30° C. After stirring for 30 min at −30° C., $CO_2$ is bubbled for 15 min at the same temperature. The mixture is brought back to −5° C. and 100 mL of water are added. THF is evaporated, the aqueous phase is extracted twice with ethyl acetate and is then acidified to pH 1. After having extracted three times with ethyl acetate, the organic phase is washed with a saturated NaCl solution, dried on $Na_2SO_4$, filtered and dry evaporated. White solid 10 g (Yield 80%).

Example 18 tert-butyl
1-Mercaptomethyl-cyclopentane-carboxylic acid
ester

The previous compound (7.9 g) is solubilized in 70 mL Of THF. At −10° C., 5.13 mL (1 equivalent) of triethylamine and 4.78 mL (1 equivalent) of isobutyl chloroformate are added. After a 2 min reaction, the formed precipitate is filtered and 4.88 g of $NaBH_4$ (3.5 equivalents) and 22 mL of MeOH are then added dropwise. The solution is brought back to 0° C. and acidified with HCl 1N. After extraction with $CH_2Cl_2$, washing and drying, the organic phase is dry evaporated. Pale yellow oil (6.52 g, Yield 88%)

The obtained alcohol (5 g) is solubilized in ether (65 mL). 2.12 mL (1.1 equivalent) of mesyl chloride and 4 mL of triethylamine are added. After stirring for 3 hrs at room temperature, the etherated phase is washed, dried and dry evaporated. Pale yellow oil (6.4 g, Yield 92%)

The mesylate (6.4 g) is solubilized in dimethylformamide (100 mL). 3.18 g of $K_2CO_3$ and 3.61 mL of thioacetic acid are added and the mixture is stirred for 5 hrs at 100° C. DMF is dry evaporated and the residue is taken up with ethyl acetate and HCl 1N. The organic phase is washed, dried and dry evaporated.

The obtained brown oil is treated with a 50/50 mixture $CH_2Cl_2$/TFA at room temperature. The mixture is dry evaporated, taken up three times with cyclohexane and dry evaporated. Rust-colored solid product (quantitative yield). The formed acetylthioacid is solubilized in 50 mL of MeOH and 50 mL of NaOH 1N is added. The mixture is stirred for 3 hrs at room temperature and then acidified with HCl 1N. The methanol is evaporated, the residue taken up with EtOAc and the organic phase is washed and dried: pale yellow oil, quantitative yield.

NMR ($CDCl_3$) δ (ppm): 1.6-1.8 (6H, m+SH), 2.15 (2H, m), 3.2 (2H, s).

Example 19

1-(2-tert-Butoxycarbonylamino-4-methyl-sulfanyl-
butyldisulfanyl-methyl)-cyclopentane-carboxylic
acid Following the procedure of Example 3 and replacing the compound of Example 1 with the compound of Example 18, the expected product is obtained. White solid, 3.8 g (yield 75%). HPLC (Kromasil Cl8, $CH_3CN$ (0.1% TFA)/$H_2O$ (0.1% TFA): 50/50) Rt 31.6 min. Mass $(M+H)^+$=410.

Example 20 di-tert-butyl 2-{[1-(2-tert-butoxycarbonyl-amino-4-
methylsulfanyl-butyldisulfanylmethyl)-cyclopen-
tane-carbonyl]-amino}-succinic acid ester Following the procedure of Example 5 and replacing the compound of Example 4 with t-butyl aspartic acid ester, the expected compound is obtained with a yield of 80%. White solid. Mass $(M+H)^+$=637.3

HPLC (Kromasil Cl8, $CH_3CN$ (0.1% TFA)/$H_2O$ (0.1% TFA): 80/20) Rt 31.6 min.

NMR ($CDCl_3$) δ (ppm): 1.4 (27H), 1.7-1.9 (8H m), 2.1 (5H m), 2.5 (2H m) 2.8-3.1 (6H m), 4.1 (1H m), 4.6 (1H m), 4.7 (1H d), 6.6 (1H d).

Example 21 di-tert-butyl 2-{[1-(2-tert-butoxycarbonyl-amino-4-
methanesulfinyl-butyldisulfanyl-methyl)-cyclopen-
tane-carbonyl]-amino}-succinic acid Following the procedure of Example 11, the compound of Example 20 leads to the expected product with a yield of 81%. Mass $(M+H)^+$=653.3

Example 22

2-({1-[2-(1-isobutyryloxy-ethoxycarbonyl-amino)-4-
methanesulfinyl-butyldisulfanylmethyl]-cyclopen-
tane-carbonyl}-amino)-succinic acid Following the procedure of Example 12, the compound of Example 21 leads to the expected final product with a yield of 63%.

HPLC (Kromasil C18 $CH_3CN$ (0.1% TFA)/$H_2O$ (0.1% TFA): 70/30) Rt 4.3 min Mass $(M+H)^+$=599.2

NMR (DMSOd6) δ (ppm): 1.0 (6H d), 1.4 (3H d), 1.7-1.9 (8H m), 2.1 (2H m), 2.5-3.0 (12H m), 3.7 (1H m), 4.6 (1H m), 6.65 (1H m), 7.5 (1H d), 8.4 (1H d).

Example 23

Pharmacological Results

The molecules of the present invention were studied for their analgesic action on the most predictive animal models for response in humans. The preferential tests are those which are intended for neuroinflammatory (NI) and neuropathic (NP) pains in rats and mice.

The molecules of the present invention proved to be active on the following tests.

In rats: i) neuropathic pain elicited by intraplantar injection of carrageenin or Freund's adjuvant (Desmeules A. et al. Pain (1993), 53, 277-285); ii) diabetic neuropathy (NP) induced by preadministration of streptozocin (Condore-Civiale et al., Br. J. Pharmacol. (2001), 67, 1301-1308); iii) neuropathy triggered by preadministration of an anti-cancer agent, vincritin (Authier et al., Neurotoxicology (2003), 4, 797-805).

In mice: i) neurophatic and neuroinflammatory allodynia and hyperalgesia induced by preadministration of tumoral cells in tibial marrow, osteosarcoma model (Menendez L. et al., Brain Res. (2003), 969, 102-109); ii) pain caused by administration of formalin in the paw and study of the analgesic response in the first phase (NT); iii) hyperalgesia and allodynia produced by partial and unilateral compression of the sciatic nerve (Seltzer's model) (Bennett G. J. and Xie Y. K., Pain (1998) 33, 87-107).

The techniques used in these tests are described in detail and classified in journals such as: M. J. Millan. The induction of pain: an integrative review, in Progress in Neurobiology (1999), 52, 1-164.

As examples, several studies will be found below.

A/Formalin Test (Phase I)

The molecules were investigated in two phases after 90 and 150 minutes in order to observe their period of action.

Description of the Test

The animals (male OF1 mice) come from the Charles River breeder (France) and weigh 25-35 g at the beginning of the experiment. The weight of each mouse is taken into account for administering the product.

The test is based on the procedure described by S. HUNSKAAR et al., Formalin test in mice, a useful technique for evaluating mild analgesics, J. Neurosci. Methods (1995), 14, 69-75.

The mice (n=8) are individually placed in a transparent enclosure (50×25 cm) and become accustomed to this environment for 20 minutes. After this period, 20 μL of formalin (5% HCHO) in solution in saline solution ($H_2O$, 0.9% NaCl), are injected subcutaneously on the plantar face of the right paw of the animal. A 26 syringe connected to a microsyringe is used. Each mouse is then immediately placed back into the test enclosure and pain (nociceptive) responses are measured for 5 minutes (early phase). Only the lickings of the paw are counted.

The analgesic activity is tested after force-feeding the animals at different times (generally 20 min, 90 min and 150 min) after injecting formalin, with:

the carrier alone (ethanol, 0.5% methylcellulose in water)
the carrier and a compound of the invention (50 mg/kg).

The analgesic action of the product is measured by the decrease in the number of lickings of the lesioned paw, as compared with the number of lickings of the animal which has received the carrier alone.

The results are shown in FIG. 1 for the six compounds of the Examples 6, 8, 10, 12, 14 and 16.

The six compounds shown potent analgesic effects (40-60%) characterized by very significant lowering of the number of lickings as compared with the carrier (control) and the effects are approximately constant during the period of the test. The analgesic action is blocked by preadministration of an antagonist, methyl-naloxonium, which, at the dose used (2 mg/kg), is incapable of crossing the blood brain barrier (Milne R. J. et al., Neurosci. Lett. (1990), 114, 25-32), demonstrating that the activity of these molecules is exerted peripherally (nociceptors) where they increase the enkephalins released at the lesioned site.

B/Comparative Study of the Analgesic Effect of the Compound of Example 6 and of the Reference Molecule (Compound 15 of the International Application Wo2007/048787)

The present invention is characterized by the development of molecules having analgesic properties at least equal to those of the compounds described in the international application WO2007/048787, but a considerably extended period of action. This is actually shown in the formalin test (the procedure of which having been described earlier) since the reference molecule:

Compound 15=$NH_2$—$CH(CH_2CH_2SCH_3)$—$CH_2$—S—S—$CH_2$—$CH(CH_2C_6H_5)$—CONH—$CH_2$—CONH—CO—$CH(CH_3)$—O—CO—$OCH_2CH_3$ (WO2007/048787) no longer has any activity at 120 minutes whereas the compound of Example 6 on the contrary attains its maximum of analgesic activity between 90 and 150 minutes (FIG. 2).

C/Antiallodynic and Antihyperalgesic Effects of the Compound of Example 10 after Oral Administration in Mice This test was described in detail by A. B. Malmberg and A. I. Basbaum, Partial sciatic nerve injury in the mouse as a model of neuropathic pain: behavioural and neuroanatomical correlates. Pain, (1998) 76, 215-222.

It was conducted on male OF1 mice (Charles River), of 18-20 g, n=39, by partial ligature of the sciatic nerve on the ipsilateral side. The animals are tested in the period (3-26 days) after the operation.

Measurement of hyperalgesia was carried out according to the method described by K. Hargreaves et al., A new sensitive method for measuring thermal nociception in cutaneous hyperalgesia, Pain, (1988), 32, 77-88, by using as a heat source, the "Plantar test" apparatus (Bioseb, France). The intensity of the nociceptive stimulus is calibrated to 8-10 s with an automatic stopping threshold (cut-off time) at 20 s. The average of the withdrawals of the paw induced by the heat, was measured on the ipsilateral paws (damaged nerve) and contralateral paws (intact nerve). This measurement was carried out 3 times on each paw. Mechanical allodynia is measured as described by S. R. Chaplan et al., Quantitative assessment of tactile allodynia in the rat paw, J. Neurosci. Meth. (1994), 53, 55-63. The ipsilateral (lesion) and contralateral (control) paws are tested as earlier. The mechanical antiallodynic effect is measured by the method of Von Frey with filaments of increasing size exerting also increasing pressure.

Antihyperalgesic Effect: FIG. 3

The results of FIG. 3 show that when administered p.o., the compound of Example 10 produces a very large significant decrease (65-100%) of thermal hyperalgesia induced by partial ligature of the sciatic nerve in the period from 45 to 150 min with a maximum effect of 100% at 80 min (8.2±0.9 s vs. 8.3 s). It is probable that the effect should still be significant at 180 min.

Anti-Allodynic Effect: FIG. 4

The effect of the compound of Example 10 on mechanical allodynia is measured by the Von Frey test. The results show a significant anti-allodynic effect of long duration with a maximum at 60 min corresponding to 75% of the maximum response (non-treated control).

BRIEF DESCRIPTION OF THE DRAWINGS

Captions of the Figures

In all the figures, the statistical analyses (p, Student's test) are indicated in the following way:

*$p<0.1$ versus control
**$p<0.01$ versus control
***$p<0.001$ versus control

Figure 1:
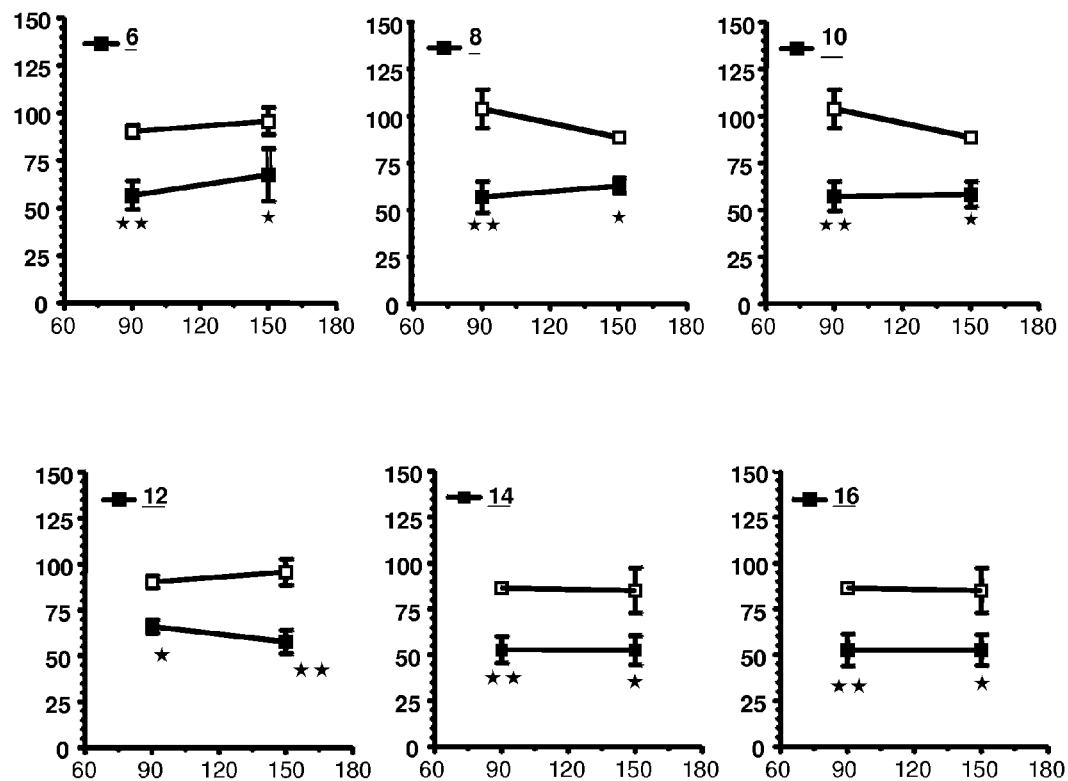

FIG. 1: number of lickings (licking, dry) of the paw versus time (minutes) after orally administering the vehicle (□) or of a compound according to the invention (■).

Abscissa: Time in Minutes; Ordinate: Number of Dry Lickings

1A: compound of Example 6; 1B: compound of Example 8; 1C: compound of Example 10; 1D: compound of Example 12; 1E: compound of Example 14; 1F: compound of Example 16.

Figure 2:
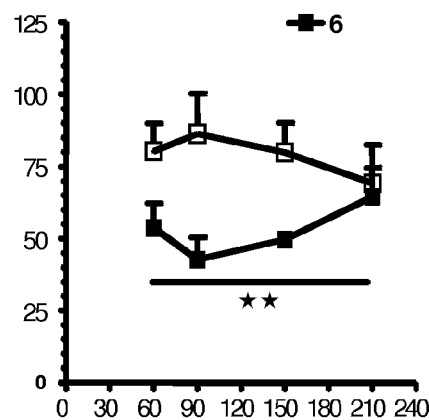
Figure 2:
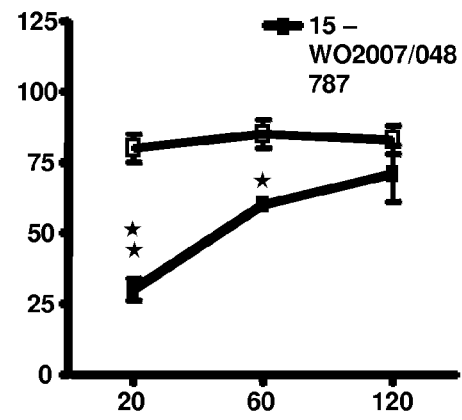

FIG. 2: number of lickings (licking, dry) of the paw versus time (minutes) after orally administering the vehicle (□) or of a compound according to the invention or a reference compound (■).

Abscissa: Time in Minutes; Ordinate: Number of Dry Lickings

Figure 3:
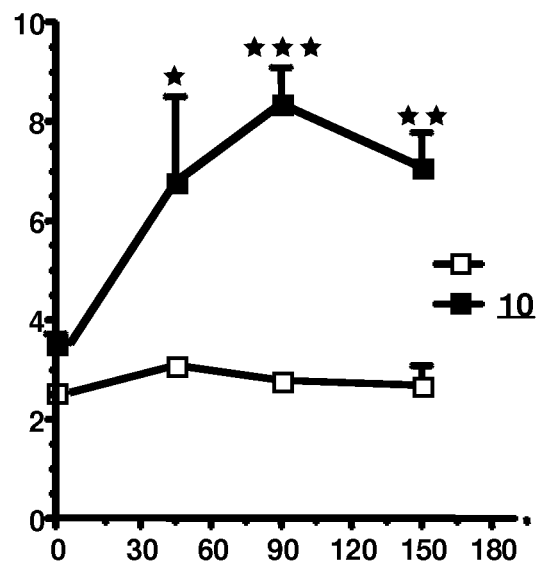

2A: compound of Example 6; 2B: compound 15 of the application WO2007/048787;

FIG. 3: Neuropathic pain model: partial ligature of the sciatic nerve (mice). Response generated by per os administration of the carrier (□) or of the compound of Example 10 (■): removal of the paw (in second) versus time (in minutes).

Compound 10: 50 mg/kg

Carrier: EtOH/0.5% methylcellulose (1.5/98.5)

Tests carried out at day 14 post-surgery; ipsilateral paw

Abscissa: time in minutes, ordinate: withdrawal of the paw in seconds

Plantar test: evaluation of thermal hyperalgia

Average of the contralateral paws: compound 10 at 90 min=8.3 s.

Figure 4:
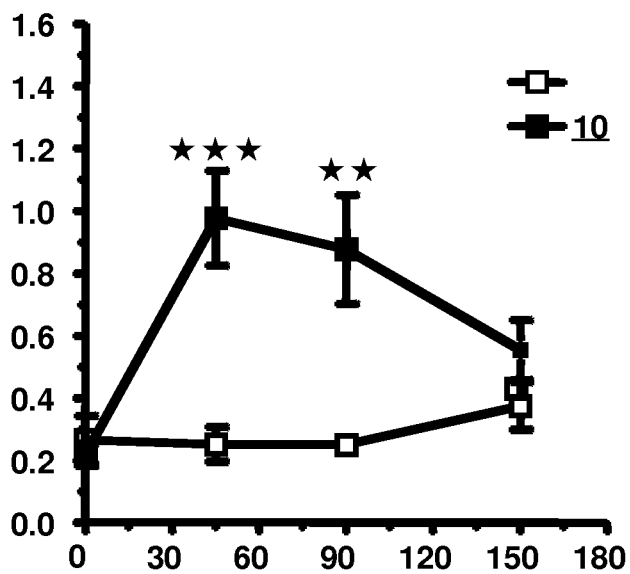

FIG. 4: Von Frey test: Von Frey pressure (g) versus time (min) after orally administering the carrier (□) or of the compound of Example 10 (■).

Compound 10: 50 mg/kg

Carrier: EtOH/0.5% methylcellulose (1.5/98.5)

Abscissa: time in minutes, ordinate: Von Frey pressure in grams.

Tests conducted on day 14 post-surgery.

The invention claimed is:

1. A compound having the following formula (I):

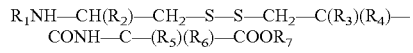

$R_1NH—CH(R_2)—CH_2—S—S—CH_2—C(R_3)(R_4)—CONH—C—(R_5)(R_6)—COOR_7$ wherein:

$R_1$ represents an (acyloxy)alkyl carbamate group

—(CO)—O—C($R_8$)($R_9$)—OC(O)—$R_{10}$, wherein $R_8$ and $R_9$ independently of each other represent a hydrogen atom, or a radical selected from the group consisting of an alkyl, aryl, arylalkyl, cycloalkyl, cycloheteroalkyl, heteroalkyl, heteroaryl and heteroarylalkyl; or taken together, $R_8$ and $R_9$ form a 5- or 6-membered cycloalkyl;

$R_{10}$ represents a radical selected from the group consisting of an alkyl, aryl, arylalkyl, cycloalkyl, cycloheteroalkyl, heteroalkyl, heteroaryl and heteroarylalkyl;

$R_2$ represents:

a linear or branched, saturated hydrocarbon chain having 1 to 6 carbon atoms; or a methylene radical substituted with a 5- or 6-membered, aromatic or saturated, heterocycle, the heteroatom being a nitrogen or sulfur atom, optionally oxidized as an N-oxide or S-oxide, wherein the linear or branched, saturated hydrocarbon chain having 1 to 6 carbon atoms is optionally substituted with OH, $OR_{11}$, SH, $SR_{11}$ or $S(O)R_{11}$, or phenyl or benzyl, wherein the phenyl or benzyl is optionally substituted with 1 to 5 halogen atoms or with a radical selected from the group consisting of OH, $OR_{11}$, SH, $SR_{11}$ or $S(O)R_{11}$, $R_{11}$, wherein $R_{11}$ is independently selected from the group consisting of a linear or branched hydrocarbon chain with 1 to 4 carbon atoms, a phenyl radical and a benzyl radical, when $R_4$ represents a hydrogen atom, $R_3$ represents:

a phenyl or benzyl radical, a 5- or 6-membered heteroaryl, the heteroatom being an oxygen, a sulfur or nitrogen atom; or a methylene group substituted a 5 or 6 members, aromatic or saturated heterocycle, the heteroatom being an oxygen, nitrogen or sulfur atom, optionally oxidized as an N-oxide or S-oxide, wherein the phenyl or benzyl radical is optionally substituted with 1 to 5 halogen atoms;

a radical selected from the group consisting of $SR_{11}$, $S(O)R_{11}$ and $OR_{11}$, $R_{11}$ having the same definition as above; or an amino group optionally mono- or di-substituted with a cyclic or linear aliphatic group having 1 to 6 carbon atoms;

or when $R_4$ is different from H, $R_3$ and $R_4$ taken together form a 5- or 6-membered saturated cycle;

$R_5$ and $R_6$ independently of each other represent:

a hydrogen atom, a linear or branched saturated hydrocarbon chain, having from 1 to 6 carbon atoms, or a phenyl or benzyl radical, wherein the linear or branched saturated hydrocarbon chain, having from 1 to 6 carbon atoms is optionally substituted with OH, $OR_{11}$, SH, $SR_{11}$, COOH or $COOR_{11}$, and the phenyl or benzyl radical is optionally substituted with a linear or branched alkyl chain with 1 to 4 carbon atoms, 1 to 5 halogens, or OH, $OR_{11}$, SH, or $SR_{11}$, wherein R is independently selected from the group consisting of a linear or branched hydrocarbon chain with 1 to 4 carbon atoms, a phenyl radical and a benzyl radical;

or taken together $R_5$ and $R_6$ from a saturated 5- or 6-membered cycle;

R7 represents a hydrogen atom;

an alkyl radical having from 1 to 4 carbon atoms;

a phenyl or benzyl radical, optionally substituted by 1 to 5 halogen atoms;

a group of formula $CR_{12}(R_{13})C(O)OR_{14}$;

a group $CR_{12}(R_{13})OC(O)R_{14}$;

a group $CR_{12}(R_{13})OC(O)OR_{14}$;

$R_{12}$ and $R_{13}$ independently of each other represent a hydrogen atom, or a radical selected from the group consisting of an alkyl, aryl, arylalkyl, cycloalkyl, cycloheteroalkyl, heteroalkyl, heteroaryl and heteroarylalkyl;

or taken together $R_{12}$ and $R_{13}$ may form a 5- or 6-membered cycloalkyl;

$R_{14}$ represents a radical selected from the group consisting of alkyl, aryl, arylalkyl, cycloalkyl, cycloheteroalkyl, heteroalkyl, heteroaryl and heteroarylalkyl; as well as the addition salts of said compound (I) with pharmaceutically acceptable mineral or organic bases and each of their enantiomers and diastereomers.

2. The compound of claim 1, wherein halogen is fluorine.

3. The compound of claim 1, wherein the radical $R_1$ represents an (acyloxy)alkyl carbamate group —(CO)—O—C($R_8$)($R_9$)—OC(O)—$R_{10}$, wherein $R_8$ and $R_9$ independently of each other represent a hydrogen atom or an alkyl group; and $R_{10}$ represents an alkyl group.

4. The compound of claim 3, wherein $R_{10}$ represents an isopropyl.

5. The compound of claim 1, wherein the radical $R_2$ represents an alkyl radical having from 1 to 4 carbon atoms, substituted with an $SR_{11}$ or $S(O)R_{11}$ radical, $R_{11}$ representing a radical selected from the group consisting of a linear or branched hydrocarbon chain with 1 to 4 carbon atoms, a phenyl radical and a benzyl radical.

6. The compound of claim 5, wherein $R_{11}$ represents a linear or branched saturated hydrocarbon chain with 1 to 4 carbon atoms.

7. The compound of claim 6, wherein $R_{11}$ is a methyl group.

8. The compound of claim 1, wherein the radical $R_4$ represents a hydrogen atom.

9. The compound of claim 8, wherein the radical $R_3$ represents:
a benzyl or phenyl radical, or
a methylene radical substituted with a 5- or 6-membered, aromatic or saturated, heterocycle, the heteroatom being a nitrogen of sulfur atom, optionally oxidized as an N-oxide or S-oxide.

10. The compound of claims 1, wherein the radicals $R_4$ and $R_3$ form together with the carbon atom which bears them, a 5- or 6-membered cycloalkyl.

11. The compound of claim 10, wherein the 5- or 6-membered cycloalkyl is a cyclopentane or a cyclohexane.

12. The compound of claim 1, wherein the radical $R_5$ represents a hydrogen atom.

13. The compound of claim 1, wherein the radical $R_6$ represents a hydrogen atom or an alkyl radical having from 1 to 6 carbon atoms, substituted with a radical selected from the group consisting of OH, SH, COOH and $COOR_{11}$, $R_{11}$ representing in each of these radicals a radical selected from the group consisting of a linear or branched hydrocarbon chain with 1 to 4 carbon atoms, a phenyl radical and a benzyl radical.

14. The compound of claim 1, wherein the radical $R_7$ represents a hydrogen atom or a radical selected from the group consisting of a phenyl, a benzyl and an alkyl radical having from 1 to 4 carbon atoms.

15. The compound of claim 1, selected from the group consisting of:
1-(1-{2-[(1-ethoxycarbonyloxy-ethoxy carbonylmethyl)-carbamoyl]-3-phenyl-propyldisulfanylmethyl}-3-methylsulfanyl-propylcarbamoyloxy)-ethyl isobutyric acid ester,
1-{1-[2-(benzyloxycarbonylmethyl-carbamoyl)-3-phenyl-propyl-disulfanylmethyl]-3-methylsulfanyl-propylcarbamoyloxy}-ethyl isobutyric acid ester,
1-{1-[2-(carboxymethyl-carbamoyl)-3-phenyl-propyl-disulfanylmethyl]-3-methylsulfanyl-propylcarbamoyloxy}-ethyl isobutyric acid ester,
1-(1-{2-[(1-ethoxycarbonyloxy-ethoxycarbonylmethyl)-carbamoyl]-3-phenyl-propyldisulfanylmethyl}-3-methane-sulfinyl-propylcarbamoloxy)-ethyl isobutyric acid ester,
1-{1-[2-benzyloxycarbonylmethyl-carbamoyl)-3-phenyl-propyl-disulfanylmethyl]-3-methanesulfinyl-propyl-carbamoyloxy}-ethyl isobutyric acid ester,
1-{1-2[2-(carboxymethyl-carbamoyl)-3-phenyl-propyl-disulfanylmethyl]-3-methanesulfinyl-propylcarbamoyl-oxy}-ethyl isobutyric acid ester,
2-({1-[2-(1-isobutyryloxy-ethoxycarbonylamino)-4-methane-sulfinyl-butyldisulfanylmethyl]-cyclopentanecarbonyl}-amino)-succinic acid,
2-({1-[2-(1-isobutyryloxy-ethoxycarbonylamino)-4-methyl-sulfanyl-butyldisulfanylmethyl]-cyclopentanecarbonyl}-amino)-succinic acid,
Benzyl 2-({1-[2-(1-isobutyryloxy-ethoxycarbonylamino)-4-methanesulfinyl-butyldisulfanylmethyl]-cyclopentanecarbonyl}-amino)-succinic acid ester, and
Benzyl 2-({1-[2-(1-isobutyryloxy-ethoxycarbonylamino)-4-methylsulfanyl-butyldisulfanylmethyl]-cyclopentanecarbonyl}-amino)-succinic acid.

16. A pharmaceutical composition, comprising at least one compound having the following formula (I):

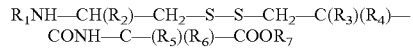

wherein:
$R_1$ represents an (acyloxy)alkyl carbamate group —(CO)—O—$C(R_8)(R_9)$—OC(O)—$R_{10}$, wherein
$R_8$ and $R_9$ independently of each other represent a hydrogen atom, or a radical selected from the group consisting of an alkyl, aryl, arylakyl, cycloalkyl, cycloheteroalkyl, heteroalkyl, heteroaryl and heteroarylalkyl; or
taken together, $R_8$ and $R_9$ form a 5- or 6-membered cycloalkyl;
$R_{10}$ represents a radical selected from the group consisting of an alkyl, aryl, arylalkyl, cycloalkyl, cycloheteroalkyl, heteroalkyl, heteroaryl and heteroarylalkyl;
$R_2$ represents:
a linear or branched, saturated hydrocarbon chain having 1 to 6 carbon atoms, or
a methylene radical substituted with a 5- or 6-membered, aromatic or saturated, heterocycle, the heteroatom being a nitrogen or sulfur atom, optionally oxidized as an N-oxide or S-oxide,
wherein the linear or branched, saturated hydrocarbon chain having 1 to 6 carbon atoms is optionally substituted with
OH, $OR_{11}$, SH, $SR_{11}$, or $S(O)R_{11}$, or
phenyl or benzyl, wherein the phenyl or benzyl is optionally substituted with 1 to 5 halogen atoms or with a radical selected from the group consisting of OH, $OR_{11}$, SH, $SR_{11}$ or $S(O)R_{11}$, $R_{11}$,
wherein $R_{11}$ is independently selected from the group consisting of a linear or branched hydrocarbon chain with 1 to 4 carbon atoms, a phenyl radical and a benzyl radical,
when $R_4$ represents a hydrogen atom, $R_3$ represents:
a phenyl or benzyl radical;
a 5- or 6-membered heteroaryl, the heteroatom being an oxygen, a sulfur or nitrogen atom; or
a methylene group substituted a 5 or 6 members, aromatic or saturated heterocycle, the heteroatom being an oxygen, nitrogen or sulfur atom, optionally oxidized as an N-oxide or S-oxide;
wherein the phenyl or benzyl radical is optionally substituted with
1 to 5 halogen atoms;
a radical selected from the group consisting of $SR_{11}$, $S(O)R_{11}$ and $OR_{11}$, $R_{11}$ having the same definition as above; or
an amino group optionally mono- or di-substituted with a cyclic or linear aliphatic group having 1 to 6 carbon atoms;
or when $R_4$ is different from H, $R_3$ and $R_4$ taken together form a saturated 5- or 6-membered cycle;
$R_5$ and $R_6$ independently of each other represent:
a hydrogen atom,
a linear or branched saturated hydrocarbon chain, having from 1 to 6 carbon atoms, or
a phenyl or benzyl radical,
wherein the linear or branched saturated hydrocarbon chain, having from 1 to 6 carbon atoms is optionally substituted with OH, $OR_{11}$, SH, $SR_{11}$, COOH or $COOR_{11}$, and the phenyl or benzyl radical is optionally substituted with a linear or branched alkyl chain with 1 to 4 carbon atoms, with 1 to 5 halogens, or with OH, $OR_{11}$, SH or $SR_{11}$, wherein $R_{11}$ is independently selected from the group consisting of a linear or branched hydrocarbon chain with 1 to 4 carbon atoms, a phenyl radical and a benzyl radical;

or taken together $R_5$ and $R_6$ from a saturated 5- or 6-membered cycle;

R7 represents a hydrogen atom;

an alkyl radical having from 1 to 4 carbon atoms;

a phenyl or benzyl radical, optionally substituted by 1 to 5 halogen atoms;

a group of formula $CR_{12}(R_{13})C(O)OR_{14}$;

a group $CR_{12}(R_{13})OC(O)R_{14}$; or a group $CR_{12}(R_{13})OC(O)OR_{14}$, $R_{12}$ and $R_{13}$ independently of each other represent a hydrogen atom, or a radical selected from the group consisting of an alkyl, aryl, arylalkyl, cycloalkyl, cycloheteroalkyl, heteroalkyl, heteroaryl and heteroarylalkyl;

or taken together $R_{12}$ and $R_{13}$ may form a 5- or 6-membered cycloalkyl;

$R_{14}$ represents a radical selected from the group consisting of alkyl, aryl, arylalkyl, cycloalkyl, cycloheteroalkyl, heteroalkyl, heteroaryl and heteroarylalkyl; as well as the addition salts of said compound (I) with pharmaceutically acceptable mineral or organic bases and each of their enantiomers or diastereomers, and a pharmaceutically appropriate excipient.

17. The composition of claim 16, wherein the excipient is appropriate for administration via an oral, nasal or intravenous route.

18. The pharmaceutical composition of claim 16, further comprising at least one compound selected from the group consisting of cannabinoids, morphine, and derivatives of Gaba selected from the group consisting of gabapentin and pregabalin.

19. The composition of claim 18, wherein the cannabinoid is $\Delta^9$-tetrahydrocannabinol.

* * * * *

UNITED STATES PATENT AND TRADEMARK OFFICE
CERTIFICATE OF CORRECTION

| | |
|---|---|
| PATENT NO. | : 8,466,309 B2 |
| APPLICATION NO. | : 12/991999 |
| DATED | : June 18, 2013 |
| INVENTOR(S) | : Marie-Claude Fournie-Zaluski, Herve Poras and Bernard Roques |

It is certified that error appears in the above-identified patent and that said Letters Patent is hereby corrected as shown below:

In the Claims

Column 24, line 28, after "R" insert --$_{11}$--.

Signed and Sealed this
Twenty-sixth Day of November, 2013

Margaret A. Focarino
*Commissioner for Patents of the United States Patent and Trademark Office*